United States Patent
Shen

(10) Patent No.: US 10,470,446 B2
(45) Date of Patent: Nov. 12, 2019

(54) ENGINEERED CELL COMPRISING A RECOMBINANT PRO-METHYLATION CIS-ELEMENT CONSTRUCT THAT RESIDES IN A REGULATORY REGION OF A TARGET GENE

(71) Applicant: Baylor College of Medicine, Houston, TX (US)

(72) Inventor: Lanlan Shen, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 161 days.

(21) Appl. No.: 15/312,986

(22) PCT Filed: May 21, 2015

(86) PCT No.: PCT/US2015/031999
§ 371 (c)(1),
(2) Date: Nov. 21, 2016

(87) PCT Pub. No.: WO2015/179660
PCT Pub. Date: Nov. 26, 2015

(65) Prior Publication Data
US 2017/0188553 A1 Jul. 6, 2017

Related U.S. Application Data

(60) Provisional application No. 62/001,803, filed on May 22, 2014.

(51) Int. Cl.
*A01K 67/027* (2006.01)
*G01N 33/50* (2006.01)

(52) U.S. Cl.
CPC ...... *A01K 67/0278* (2013.01); *A01K 67/0275* (2013.01); *G01N 33/5088* (2013.01); *A01K 2217/072* (2013.01); *A01K 2267/03* (2013.01); *A01K 2267/0331* (2013.01)

(58) Field of Classification Search
CPC ............ A01K 67/0278; A01K 67/0275; A01K 2217/072; A01K 2267/0331; G01N 33/5088
See application file for complete search history.

(56) References Cited

U.S. PATENT DOCUMENTS

2012/0164110 A1* 6/2012 Feinberg ............. C12Q 1/6881
424/93.7

FOREIGN PATENT DOCUMENTS

WO 1999/050403 A2 10/1999
WO 2003/025175 A2 3/2003

OTHER PUBLICATIONS

Cheung et al. "Genome-wide DNA methylation profiling reveals novel epigenetically regulated genes and non-coding RNAs in human testicular cancer." Br J Cancer. Jan. 19, 2010;102(2):419-27. (Year: 2010).*
Zhang, Yan, "Identification of Factors Involved in DNA Methylation of CPG-Island-Promoters" (2011). UT GSBS Dissertations and Theses (Open Access). 182 (Year: 2011).*
Zhang et al., "Repetitive Elemetns and Enforced Transcriptional Repression Co-operate to Enhance DNA Methylation Spreading Into a Promoter CpG-island," Nucleic Acids Research, May 17, 2012, vol. 40, No. 15; pp. 7257-7268.
Hochedlinger et al. "Reprogramming of a Melanoma Genome by Nuclear Transplantation," Genes Dev, Aug. 1, 2004, vol. 18, No. 15, pp. 1875-1885.
Yu et al., "Targeted p16Ink41 Epimutation Causes Tumorigenesis and Reduces Survival in Mice," The Journal of Clincal Investigation, Jul. 25, 2014, vol. 124, No. 9; pp. 3708-3712.

* cited by examiner

*Primary Examiner* — Titilayo Moloye
(74) *Attorney, Agent, or Firm* — Norton Rose Fulbright US LLP

(57) ABSTRACT

Embodiments of the disclosure concern compositions and methods for genetic engineering related to hypermethylation of sequences. In particular embodiments, there are methods and compositions to induce DNA methylation in a manner that leads to transcriptional suppression of a target gene that allows characterization of the gene and/or its expression.

30 Claims, 31 Drawing Sheets

Specification includes a Sequence Listing.

5'ATCCCAGCTACTTGGGAGGCTGAGGCAGGAGAATCACGGAGAATCACGGATCCAGCCTGGCCAA CATGGTGAAAACCCGTCTCTACTAAAAATACAAAAATTAAAGCTTAGATCGTGTCA CTGCACTCCAGCCTGGGTGACAGAGCAAGA 3'

FIG. 4C

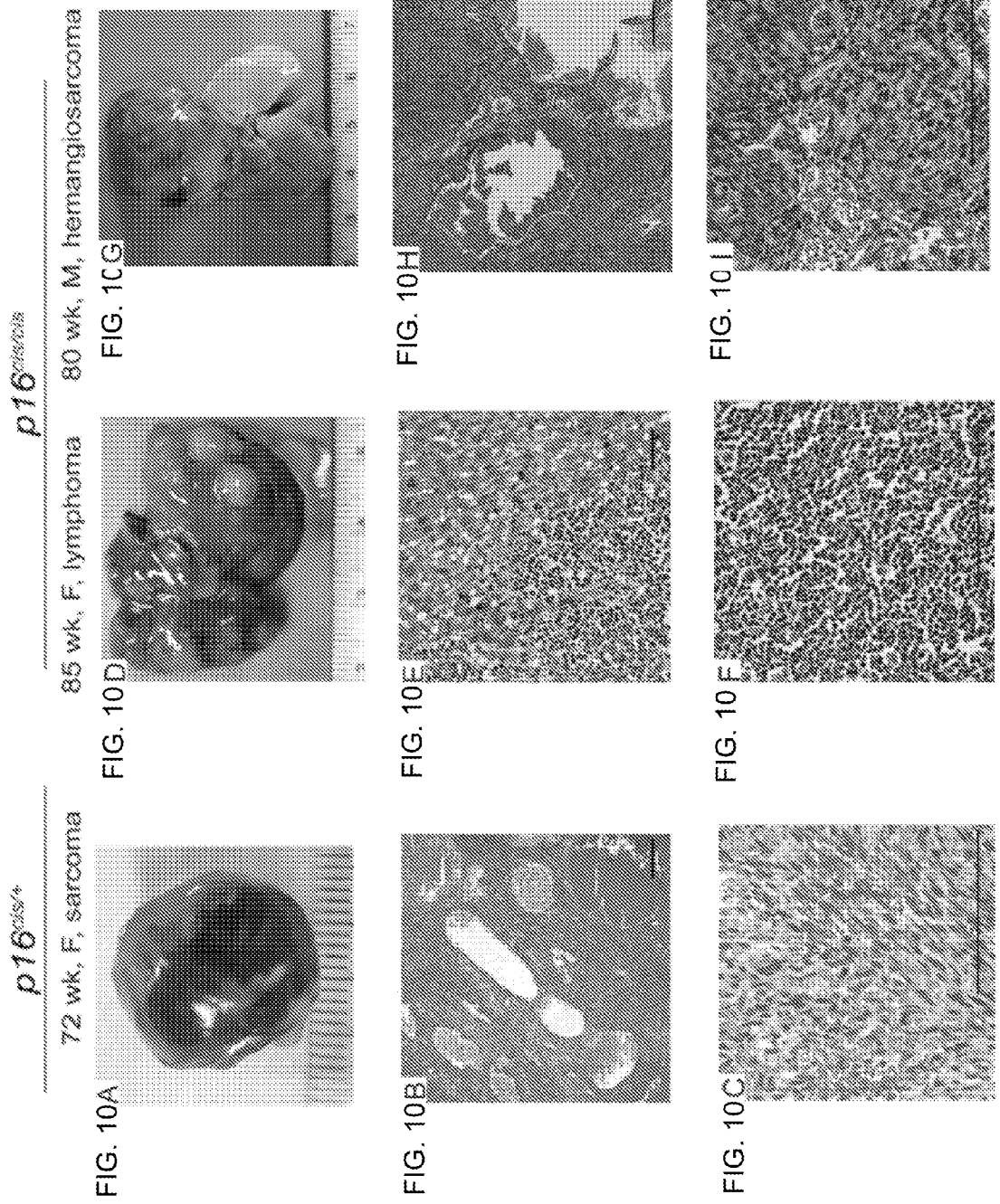

FIG. 11A M, 53wk, lung carcinoma

FIG. 11D F, 53wk, angiosarcoma

FIG. 11G M, 59wk, sarcoma p16$^{cis/+}$

ENGINEERED CELL COMPRISING A RECOMBINANT PRO-METHYLATION CIS-ELEMENT CONSTRUCT THAT RESIDES IN A REGULATORY REGION OF A TARGET GENE

CROSS REFERENCE TO RELATED APPLICATIONS

This application is a national phase application under 35 U.S.C. § 371 that claims priority to International Application No. PCT/US2015/031999 filed May 21, 2015, which claims priority to U.S. Provisional Patent Application Ser. No. 62/001,803, filed May 22, 2014, all of which are incorporated by reference herein in their entirety.

STATEMENT REGARDING FEDERALLY SPONSORED RESEARCH OR DEVELOPMENT

This invention was made with government support under CRIS 6250-51000-055-50S awarded by the U.S. Department of Agriculture. The government has certain rights in the invention.

TECHNICAL FIELD

Embodiments of the disclosure relate at least to the fields of cell biology, molecular biology, genetic engineering, and medicine.

BACKGROUND OF THE INVENTION

More than 25 years ago it was proposed that epimutation—mitotically stable gene silencing associated with epigenetic alteration in DNA methylation—can act as one of Knudson's two hits required for tumorigenesis (1). In subsequent decades many promoter CpG island (CGI) associated genes have been shown to be aberrantly hypermethylated and silenced in various cancers (2). Indeed, recent epigenomic studies revealed that nearly all tumor types harbor hundreds of abnormally hypermethylated promoter CGIs (3), indicating that epimutations are as common in tumors as genetic mutations. Aberrant promoter CGI methylation is associated with distinct environmental exposures (4), gene mutation patterns (5), cancer prognosis (6) and response to therapy (7). Despite the undisputed importance of DNA methylation in cancer, however, its fundamental role in carcinogenesis remains unclear (8-9). Most importantly, it remains unknown whether aberrant DNA methylation is a cause of tumorigenesis (8).

Cancer-related promoter CGI hypermethylation originates in normal tissues, suggesting aberrant methylation could predispose to malignancy (10). $p16^{INK4A}$ (referred to hereafter as p16) is a tumor suppressor gene that regulates the ability of retinoblastoma (RB) protein to control exit from the G1 stage of the cell cycle (11). Inactivation of p16 by promoter CGI methylation is one of the most common and earliest epigenetic events in human cancer (12), and is frequently detected in preneoplastic lesions (13-15). Mice provide an apt model in which to study epigenetic dysregulation of p16 in cancer; in a mouse model of chemically-induced lung cancer, p16 methylation is a very early event (16). Moreover, p16 age-associated hypermethylation is observed in several normal human and mouse tissues (17-19). Together, these data suggest that epigenetic silencing of p16 in aging cells facilitates early abnormal clonal expansion, driving tumorigenesis (20). Directly testing this hypothesis, however, requires the ability to specifically target methylation to the p16 promoter CGI.

BRIEF SUMMARY OF THE INVENTION

The present disclosure is directed to a system, methods, and compositions that generally relate to genetic engineering to ascertain gene function in a cell or organism. In particular embodiments, recombinant sequences are employed to induce a non-natural state, such as a non-natural methylation state, for a gene and/or its regulatory sequence(s), thereby rendering the expression of the gene reduced in part or in full. The reduction in expression of the gene allows one to determine the function of the gene by assaying for at least one characteristic of the cell or organism in the absence of the gene function.

In specific embodiments of the disclosure, one or more sequences that facilitate an increase in methylation at and/or surrounding the sequences are employed in a regulatory region of the gene. In certain aspects, one or more sequences that recruit one or more enzymes to increase CpG methylation are employed in a regulatory region of the gene. In particular embodiments, the sequences are located in a regulatory region of a gene, such as a promoter, for example, although the regulatory region and the sequences may be located in one or more regulatory regions of the gene that are not the promoter, such as an intron. In particular embodiments, the sequences that facilitate an increase in methylation are referred to as being, or being comprised in, pro-methylation cis element constructs, and in at least some cases such cis elements recruit one or more endogenous DNA methyltransferases to the regulatory region to facilitate methylation, including hypermethylation. Such elements may have one or more moieties present. In particular cases, the construct includes not only one or more sequences that recruit DNA methyltransferase(s) (such as DNMT1, DNMT2, DNMT3a, or DNMT3b) but the element may also have one or more sequences to allow stable incorporation of the construct in the genome of the cell.

Embodiments of the disclosure in a specific example show that targeted $p16^{Ink4a}$ epimutation causes tumorigenesis in mice in vivo utilizing methods as described herein. Other genes may analogously be targeted.

In particular embodiments of the disclosure, the pro-methylation cis-element is inserted within about 1500, 1250, 1000, 900, 800, 700, 750, 600, 500, 400, 300, 200, or 100 base pairs upstream of the transcription start site.

In one embodiment of the disclosure, there is an engineered cell comprising a recombinant pro-methylation cis-element construct, wherein said element resides in a regulatory region of a target gene. In a specific embodiment, the cis-element comprises SEQ ID NO:1, SEQ ID NO:3, SEQ ID NO:4, or a combination thereof. In some cases, the cis-element comprises sequence that is at least 80%, 85%, 90%, 95%, 97%, or 99% identical to SEQ ID NO:1; and/or the cis-element comprises sequence that is at least 80%, 85%, 90%, 95%, 97%, or 99% identical to SEQ ID NO:3; and/or the cis-element comprises sequence that is at least 80%, 85%, 90%, 95%, 97%, or 99% identical to SEQ ID NO:4; and/or the cis-element comprises SEQ ID NO:6; and/or the cis-element comprises sequence that is at least 80%, 85%, 90%, 95%, 97%, or 99% identical to SEQ ID NO:6. In a specific embodiment, the cell is a mammalian cell, a stem cell, an embryonic stem cell, a somatic cell, or a germ cell. In a particular case, the cell is not a cell of the testis or sperm. In some cases, the construct comprises site-directed recombination elements, such as Cre-Lox elements, Flp-FRT elements, PKG-Em7-Neo, or a combination thereof. In particular embodiments, the construct lacks sequence that encodes a DNA methyltransferase. In one embodiment, there is a plurality of any of cells described herein.

In one embodiment, there is a non-human transgenic animal comprising one or more cells that harbor a recombinant pro-methylation cis-element construct that resides in a regulatory region of a target gene. In a specific embodiment, the animal is a mouse. The construct may comprise site-directed recombination elements.

In one embodiment, there is a method of characterizing a gene function or characterizing expression of a gene, comprising the steps of reducing the expression of the gene in a cell by inducing hypermethylation of a regulatory sequence of the gene wherein the sequence is not normally methylated. In a specific embodiment, the reducing step is further defined as inserting a recombinant pro-methylation cis-element construct in a regulatory region of the gene; and assaying for a change in expression level of the gene or assaying for a characteristic of the cell or gene product. In a certain case, the characteristic is the presence or absence of cancer. In one embodiment, the assaying step comprises assaying for the presence or absence of promoter methylation. In a specific aspect, the assaying step comprises assaying for gene silencing. In a specific embodiment, the cell is a somatic cell or a neuron. In some cases, the method occurs in vitro or in vivo. In specific embodiment, the inducing of hypermethylation of a regulatory sequence of the gene comprises recruitment of one or more endogenous DNA methyltransferases to the cis-element.

In one embodiment, there is a method of associating a gene product with a disease in an individual, comprising the steps of inserting in at least one cell of an individual a recombinant pro-methylation cis-element construct in a regulatory region of a gene suspected of being associated with the disease; and assaying for a change in a characteristic of the cell or a gene product of the gene, wherein when there is a change in the characteristic or gene product that results in one or more symptoms of the disease in the individual, the gene product is associated with the disease. In a specific embodiment, the disease is cancer, a neurological disease, congenital disease, cardiovascular disease, obesity and type 2 diabetes, neurological or psychiatric disorders.

In a specific embodiment, the cis element acts through recruitment of DNMT3L and/or DNMT3A, and in particular embodiments the recruitment occurs at the stage when de novo methylation occurs.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

(FIG. 1C) Examples of bisulfite-pyrograms of 3 CpG sites between −615 bp to −589 bp in $p16_{+/ctr-neo}$ (left panel) and $p16_{+/cis-neo}$ (right panel) mESCs before and after differentiation. (FIG. 1D) Clonal bisulfite-sequencing analysis of 11 CpG sites between −814 bp to −589 bp relative to TSS confirms essentially no promoter methylation in undifferentiated $p16_{+/cis-neo}$ ESCs (top). In contrast, extensive methylation was found in differentiated $p16_{+/cis-neo}$ cells (bottom). Each row represents an individual clone. Circles represent CpG sites; open (unmethylated) and filled (methylated). (FIG. 1E) Quantitative p16 gene expression analysis shows strong transcriptional suppression in differentiated $p16_{+/cis-neo}$ cells compared with controls. Values are given as means and standard errors of the mean (SEM). **P<0.01 by Student's t test.

(FIG. 2A) CpG maps and regions assayed for DNA methylation. (FIG. 2B) DNA methylation profiling in multiple tissues from $p16_{cis}$ homozygous mice (n=2) at birth. (FIG. 2C) Comparison of methylation profiling in the spleens obtained from $p16_{cis/cis}$ mice at birth (P0) and at age 40 week (wk) (n=2-4 per age). (FIG. 2D) Significant age-associated increases in DNA methylation in multiple tissues from $p16_{cis/cis}$ mice (n=3-4 per group). Shown are average methylation levels at promoter CpGs between −814 bp to −589 bp relative to TSS. (FIG. 2E) Expression analysis shows significantly reduced p16 transcription in the tissues from 40 wk-old $p16_{cis/cis}$ mice (n=3-4 per group). * P<0.05 and **P<0.01 by Student's t test; error bars are ±SEM.

(FIG. 3C) Kaplan-Meier survival analysis indicates that $p16_{cis/−}$ mice have a significantly shortened lifespan. (FIG. 3D) Quantitative DNA methylation analysis revealed significantly increased p16 promoter methylation in the bulk of tumor tissues collected. Tumor 1 and 2 (T1 and T2) were collected from the same $p16_{cis/cis}$ mouse with metastatic lymphoma in the liver and spleen respectively, T3 was collected from the $p16_{+/cis}$ mouse, and T4 and T5 were collected from two individual $p16_{cis/−}$ mice. Dotted line (ctr, grey) indicates the average levels of methylation (±SEM) in multiple age-matched control tissues (N=4). (FIG. 3E) Immunohistochemical analysis demonstrated that promoter hypermethylation resulted in abrogation of p16 protein expression in tumor cells. (i) A lymphoma with p16 promoter hypermethylation. (ii) A positive control skin tissue showing strong immunostaining Scale bars, 100 μm. (FIG. 3F) Proposed model for a direct role of developmentally regulated p16 methylation in tumorigenesis.

FIGS. 4A-4C: DNA sequence motifs significantly enriched in genes with methylated promoter CGIs. (FIG. 4A) Sequence logos represent the consensus sequence for each of three candidate motifs. The +/− signs indicate presence in forward and reverse DNA strands, respectively. (FIG. 4B) Occurrences and positions of the motifs flanking the center of the indicated methylated promoter CGIs (green bar). (FIG. 4C) Insertion construction of a 140 bp DNA sequence element which comprises the top three identified motifs.

(FIG. 5A) Map of pHyg-G5-eGFP vector. (FIG. 5B) Map of linearized plasmid with cis-element inserted in front of targeted promoter. (FIG. 5C) CpG maps of the two constructs without (w/o) or with (w) cis-element. (Vertical lines indicate CpG sites.) The locations of methylation assays for both bisulfite-pyrosequencing (Bis-Pyro) and clonal bisulfite-sequencing (Bis-Seq) are indicated below. (FIG. 5D) Quantitative methylation analysis by bisulfite-pyrosequencing at various time-points after transfection. Results are shown from 3 independent experiments. Significantly increased methylation was found in constructs including the cis-element. (FIG. 5E) Clonal bisulfite sequencing confirms that the cis-element induces methylation at 60 days after transfection. Each row represents an individual cloned allele. Circles represent the location of CpG sites; open circles represent unmethylated cytosines, and filled circles indicate methylation. The 29 CpGs assayed were specific to the constructs; the first 19 CpG sites from left to right are located within the INSL6 promoter CGI, and the last 10 are within the vector sequence (FIG. 6A) CpGs assayed for DNA methylation. (FIG. 6B) DNA methylation kinetics of transgenes (with or without cis-element) was determined by quantitative bisulfite-pyrosequencing at region 2. (FIG. 6C) Bisulfite-sequencing confirms that cis-element induces methylation at 80 days after selection. The induced de novo methylation extends both 5' (region 1) and 3' (>1 kb away, region 2) from the cis-element. (FIG. 6D) FACS analyses shows cis-element reduces the p16 transgene expression at day 80 after selection.

(FIG. 7A) Genomic structure of mouse p16 locus. The exons 1α (p16$_{Ink4a}$) and 1β (p19$_{Arf}$) are separated by >11 kb. Red arrow indicates the knock-in site. (FIG. 7B) Targeting strategy to insert either cis- or control (ctr) elements 1 kb upstream of p16 promoter. Schematic diagram showing structures of targeting vector, wild-type (WT) p16 allele, targeted p16$_{cis-neo}$ or p16$_{ctr-neo}$ allele, p16$_{cis}$ or p16$_{ctr}$ allele after Flp mediated recombination and p16$_{lox}$ allele after Cre mediated recombination. The crossed broken lines indicate the areas of homology. Digestion with BamHI distinguishes the targeted allele from the WT allele. The neomycin resistant cassette is flanked by Frt sequences and the inserted cis- or ctr-elements are flanked by LoxP sequences. (FIG. 7C) Southern blot analysis. The expected sizes of wild type (+) (14.4 kb) and p16 gene-targeted (cis-neo) bands (11.4 kb for 5' probe and 5.0 kb for 3' probe) are shown. (FIG. 7D) Germline transmission of targeted p16$_{cis-neo}$ allele. Left panel: the male chimera and his agouti offspring. Right panel: PCR genotyping of the wild-type (WT) and p16 gene-targeted (KI) alleles. M, 100 bp DNA marker; 1 and 4 are p16$_{cis-neo}$ positive offspring; and 2, 3, 5 and 6 are the germline-negative offspring.

FIGS. 10A-10I: Gross appearance and histology of tumors collected from one p16$_{cis/+}$ (FIG. 10A-FIG. 10C) and two p16$_{cis/cis}$ (FIG. 10D-FIG. 10I) mice. The age and sex of each animal are indicated. (FIG. 10A-FIG. 10C): A sarcoma arising from the neck region. (FIG. 10D-FIG. 10F): A hepatic lymphoma metastasis. (FIG. 10G-FIG. 10I): A liver hemangiosarcoma. Scale bars equal 200 μm.

FIGS. 11A-11I: Gross appearance and histology of tumors collected from p16$_{cis/−}$ mice. The age and sex of each animal are indicated. (FIG. 11A-FIG. 11C): a lung papillary carcinoma. (FIG. 11D-FIG. 11F): an angiosarcoma arising from the rear leg. (G-I): a sarcoma arising from the tailbone. Scale bars equal 200 μm.

DETAILED DESCRIPTION OF THE INVENTION

Figure 1A:
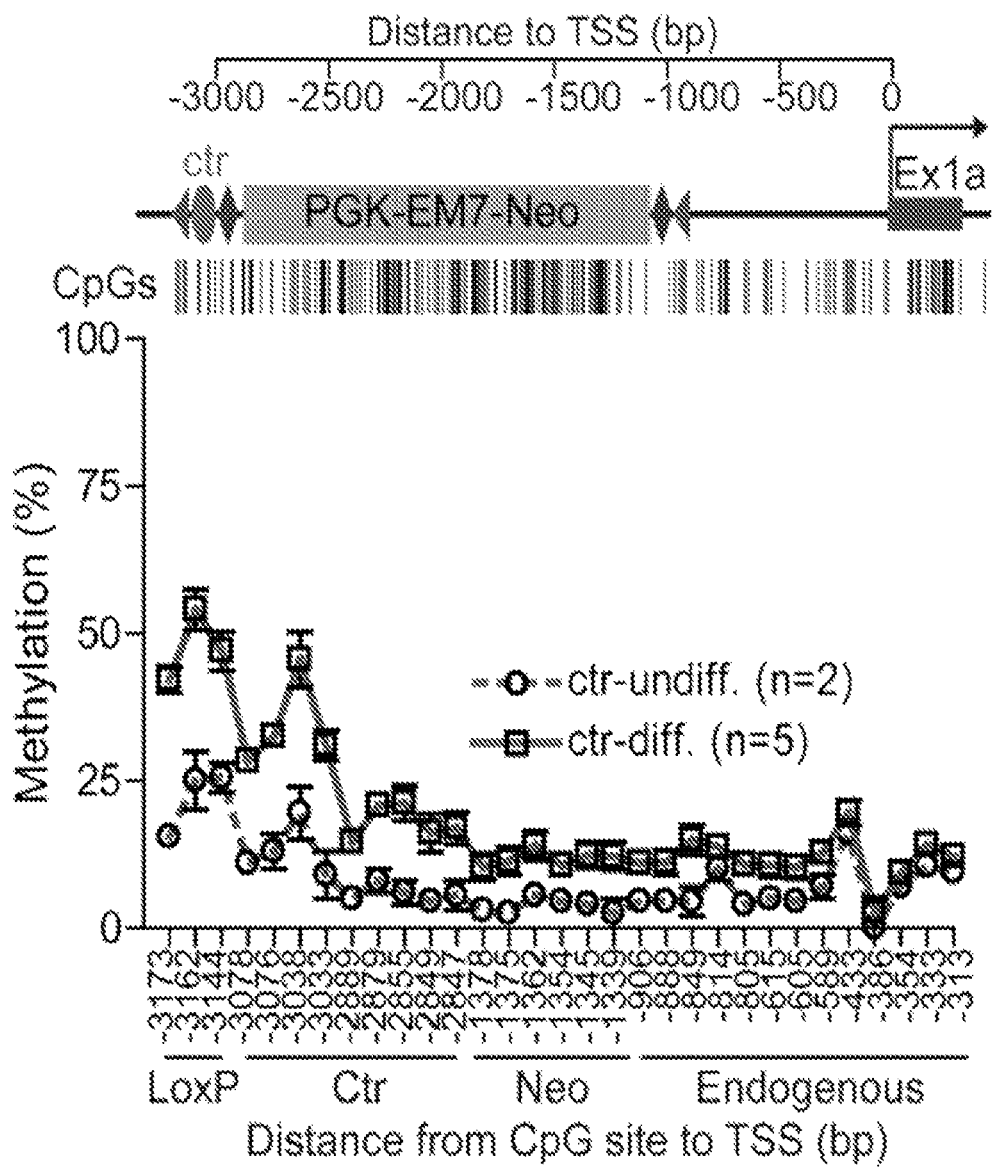
FIGS. 1A-1E: Cis-element specifically induces p16 promoter methylation. Quantitative DNA methylation profiling in $p16_{+/ctr-neo}$ (FIG. 1A) and $p16_{+/cis-neo}$ (FIG. 1B) mESCs before and after differentiation. The top of each panel shows a schematic of the p16 promoter of targeted alleles, including CpG maps.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein embodiments which are disclosed and still obtain a like or similar result without departing from the spirit and scope of the invention.

Hypermethylation of promoter CpG island (discrete genomic regions of high CpG density) and associated gene inactivation have been extensively studied, particularly in cancer. Remarkably, however, it remains unclear whether aberrant hypermethylation plays a causal role in cancer. An experimental approach to test whether hypermethylation is indeed a cancer-causing "driver" is urgently needed to advance the field of cancer epigenetics, at least.

Embodiments of the disclosure provide methods and compositions that focus hypermethylation at one or more specific sites in the genome of a cell, wherein the hypermethylation of the one or more sites provides information about the function of the sites (the site may be a gene and/or regulatory region). In specific embodiments, the compositions of the disclosure are utilized to determine if the reduction in expression of one or more genes results in a detectable outcome, and when the outcome is detected, the gene can be said to be associated with the outcome. In specific embodiments, the cell is a somatic cell and the outcome is the presence or absence of cancer.

Embodiments of the disclosure provide a novel mouse model using epigenetic engineering to directly test whether promoter CpG island methylation, without genetic mutation, drives a particular pathway, such as for tumorigenesis, obesity, or cardiovascular disease, for example. Such subject matter builds upon work that identified specific cis-elements associated with programmed promoter CpG island methylation during normal development. The disclosure provides experimental confirmation that juxtaposition with a "pro-methylation" cis-element is sufficient to induce promoter CpG island methylation both in vitro and in vivo. This functionally validated cis-element provides a unique tool to exogenously target hypermethylation to specific genomic loci. There is demonstrated herein the feasibility of such epigenetic targeting at a known tumor suppressor gene promoter, $p16^{Ink4a}$, in mice. This provides better understanding of epigenetic dysregulation in cancer and establishes a new paradigm for epigenetic research.

Long viewed as a genetic disease, cancer frequently involves epigenetic silencing associated with aberrant promoter DNA methylation, suggesting it is also an epigenetic disease. It has remained unresolved, however, whether an aberrant change in epigenetic regulation—an 'epimutation'—can induce tumorigenesis. In embodiments of the disclosure, there is exploitation of a functionally validated cis-acting regulatory element that allowed development of a strategy to induce developmentally regulated genomic targeting of DNA methylation. This system was employed to target DNA methylation to the $p16^{Ink4a}$ promoter in mice in vivo. Engineered $p16^{Ink4a}$ promoter hypermethylation leads to transcriptional suppression in somatic tissues during aging and increased incidence of spontaneous cancers. Further, mice carrying a germline $p16^{Ink4a}$ mutation on one allele and somatic epimutation on the other had accelerated tumor onset and significantly shortened tumor-free survival. Taken together, these results provide direct functional evidence that $p16^{Ink4a}$ epimutation drives tumor formation and malignant progression and demonstrates a novel approach to epigenetic engineering.

I. Pro-Methylation Cis Element

Figure 4A:
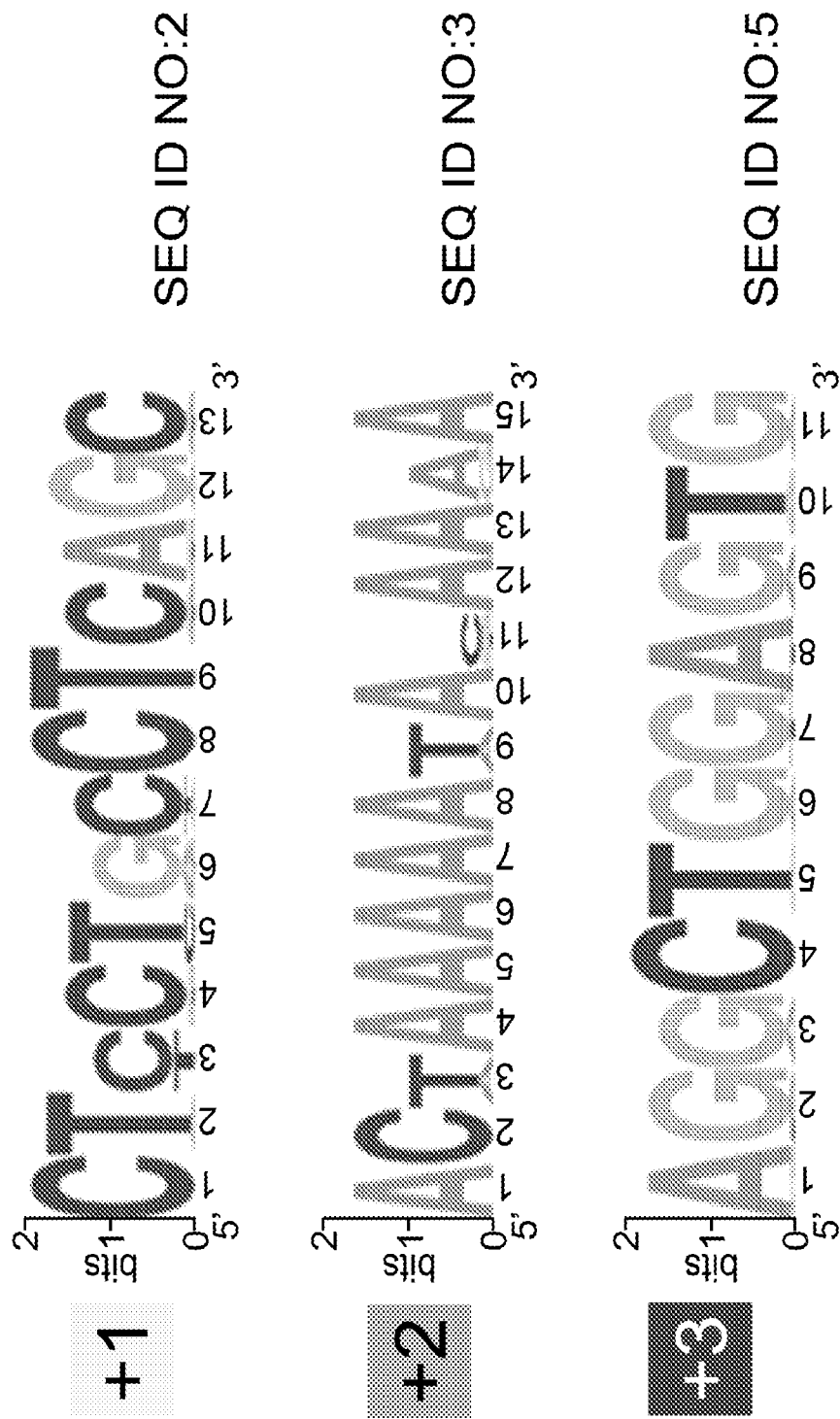

Embodiments of the disclosure concern the composition and use of the composition that comprises a pro-methylation cis-element. In specific embodiments, the element is on a nucleic acid construct, such as a construct that comprises one or more moieties other than the cis elements. In specific cases, the construct comprises one or more of SEQ ID NO:1, SEQ ID NO:3, and SEQ ID NO:4:

```
SEQ ID NO: 1:
GCTGAGGCAGGAG (which is the reverse complement
of SEQ ID NO: 2 listed in FIG. 4A).

SEQ ID NO: 3:
ACTAAAAATACAAAA

SEQ ID NO: 4:
CACTCCAGCCT (which is the reverse complement of
SEQ ID NO: 5 listed in FIG. 4A)
```

In particular embodiments, the construct comprises the following, wherein SEQ ID NO:1 is underlined, SEQ ID NO:3 is double underlined, and SEQ ID NO:4 has a dotted line underneath:

---

(SEQ ID NO: 6)

ATCCCAGCTACTTGGGAG<u>GC TGAGGCAGGAG</u>AATCACGGA

TCCAGCCTGGCCAACATGGTGAAAACCCGTCTCT<u>ACTAAAA</u>

<u>ATACAAAA</u>ATTAAAGCTTAGATCGTGTCACTGC<u>ACTCCAGC</u>

<u>CT</u>GGGTGACAGAGCAAGA.

---

In specific cases, the pro-methylation comprises sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to the sequence of SEQ ID NO:1, SEQ ID NO:3, SEQ ID NO:4, or SEQ ID NO:6.

In specific embodiments, the sequence of the cis-element is positioned within the element and in the appropriate orientation to be able to recruit one or more DNA methyltransferases (such as by binding the cis-element sequence directly or indirectly).

In particular embodiments, the pro-methylation cis-element further comprises one or more elements that facilitate stable integration into the genome of a cell. In specific cases, the elements facilitate site-directed recombination, including homologous recombination. In some cases, the construct comprises sequence homologous to the sequence 5' to the site of insertion, cis element, marker, and sequence homologous to the sequence 3' to the site of insertion. In specific embodiments, a recombinogenic fragment may comprise the following (5' to 3'): about 200 bp sequence homologous to the sequence 5' to the site of insertion, cis-element, Frt, Neomycin selection cassette, Frt, and about 200 bp sequence homologous to the sequence 3' to the site of insertion.

In specific cases, the construct comprises a detectable marker, such as one that provides antibiotic resistance, is fluorescent, and so forth. Examples include GFP and lacZ.

In specific embodiments, LoxP sites (or analogous elements) flank the cis-element, which will allow the conditional deletion of cis-element.

II. Transgenic Non-Human Animals

Transgenic non-human animals (e.g., mammals) of the disclosure can be one or more of a variety of species including murine (rodents (e.g., mice, rats), avian (chicken, turkey, fowl), bovine (beef, cow, cattle), ovine (lamb, sheep, goats), porcine (pig, swine), and piscine (fish). In a preferred embodiment, the transgenic animal is a rodent, such as a mouse or a rat.

Transgenic gene constructs can be introduced into the germ line of an animal to make a transgenic mammal. For example, one or several copies of the pro-methylation cis-element construct may be incorporated into the genome of a mammalian embryo by standard transgenic techniques.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor.

Introduction of the transgene into the embryo can be accomplished by any means known in the art such as, for example, microinjection, electroporation, or lipofection. For example, the Fc receptor transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

The progeny of the transgenically manipulated embryos can be tested for the presence of the construct by Southern blot analysis of the segment of tissue. If one or more copies of the exogenous cloned construct remains stably integrated into the genome of such transgenic embryos, it is possible to establish permanent transgenic mammal lines carrying the transgenically added construct.

The litters of transgenically altered mammals can be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those mammalian progeny found to contain at least one copy of the construct in their genome are grown to maturity.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures.

The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of an Fc receptor. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) Nature 292:154-156; Bradley et al. (1984) Nature 309:255-258; Gossler et al. (1986) PNAS 83: 9065-9069; and Robertson et al. (1986) Nature 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468-1474.

III. Kits of the Disclosure

Any of the compositions described herein may be comprised in a kit. In a non-limiting example, a cell(s), nucleic acid, and/or reagents to manipulate a cell and/or nucleic acid may be comprised in a kit. The kits may thus comprise, in suitable container means, nucleic acids, enzymes, buffers, cells, and so forth to perform methods of recombinantly introducing a pro-methylation cis-element construct and/or generating the construct. In specific embodiments, nucleic acids that comprise SEQ ID NO:1, SEQ ID NO:2, SEQ ID NO:3, SEQ ID NO:4, SEQ ID NO:5, or SEQ ID NO:6, or nucleic acids that target one of these sequences or that amplify one of these sequences, may be included in the kit. Examples of enzymes include polymerases, ligases, restriction enzymes, and so forth. One or more cells for manipulation may be included in the kit, including prokaryotic (such as E. coli) or eukaryotic cells. In some embodiments, reagents or apparatus(es) to assay for a characteristic of a cell or organism are included, such as reagents to facilitate identification of cancer, for example, such as antibodies, dyes, and so forth. In some cases, there are reagents for sensitive and quantitative methylation detection by bisulfite-pyro sequencing, for example.

The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the component(s) in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

In particular embodiments, an apparatus to remove a sample from an individual may be included, such as a scalpel, swab, syringe, and so forth.

Example 1

Targeted P16$^{Ink4a}$ Epimutation Causes Tumorigenesis in Mice In Vivo

Figure 4B:
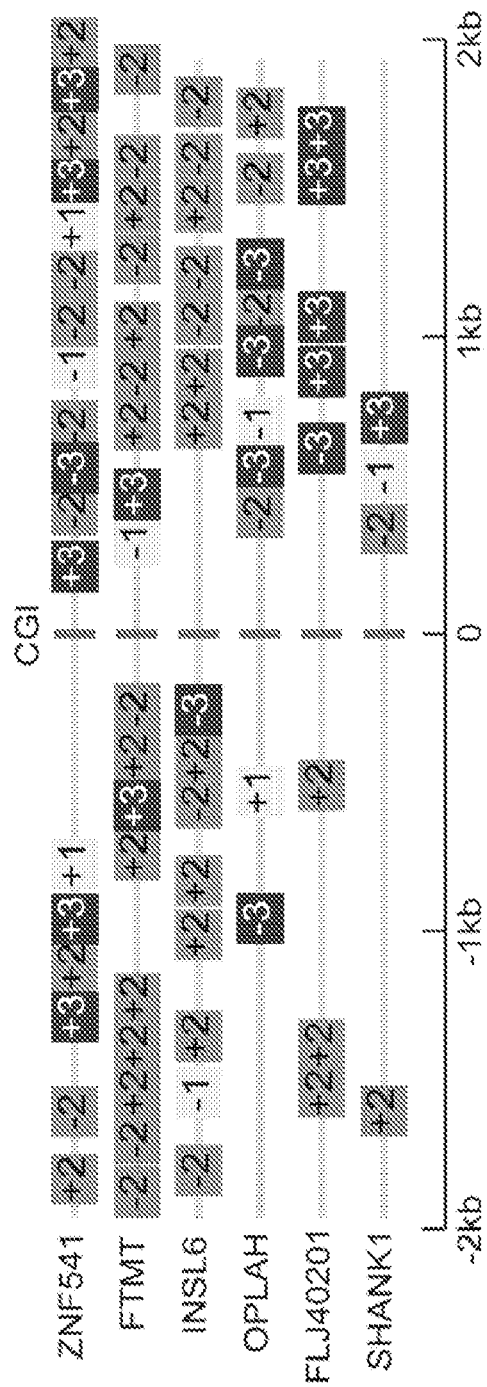

Cis-acting DNA sequences are important for the establishment of genomic patterns of DNA methylation (21-22). A cis-element was engineered to attract DNA methyltransferases (DNMTs) during development to achieve targeted de novo DNA methylation in vivo. Subject matter of the disclosure built upon the demonstration that an exceptional class of promoter CGIs that are methylated and silenced in normal somatic tissues is associated with specific cis-acting DNA motifs (23). To test the function of the identified motifs in vitro, a 140 base-pair (bp) cis-element was constructed containing the top three DNA motifs in the order and orientation most frequently observed in the normally methylated CGIs (FIG. 4). A stable integrated system was used to test transgenes targeting two human promoter CGIs, one at INSL6 and another at p16, during 80 days in cell culture using both human (LNCaP) and mouse (NIH3T3) cell lines. The cis-element induced extensive and progressive de novo methylation throughout the promoter CGIs of the juxtaposed transgenes (FIGS. 5 and 6). These positive results prompted generation of a mouse model with targeted knock-in of the pro-methylation cis-element at the p16 locus.

The cis-element was introduced ~1 kb upstream of p16 transcription start site (TSS) in mouse embryonic stem cells (mESCs) through homologous recombination (FIG. 7). The insertion leaves the p16 core promoter intact and avoids affecting the p15$^{Ink4b}$, p15 antisense (p15AS) and p19$^{Arf}$ promoters located >27 kb, >12 kb and >11 kb away, respectively (FIGS. 7A and 7B). As a negative control for insertion effects, the effects were compared of the cis-element against those of an Alu sequence located ~1 kb upstream of human p16, since this Alu shows no sequence homology to the cis-element, and site-specific integration of this repetitive element does not affect methylation at neighboring genes (24). Germline transmission of both the control and cis elements was achieved and confirmed by Southern blotting (using both 5' and 3' probes, FIG. 7C), PCR (FIG. 7D) and DNA sequence analysis.

Figure 1B:
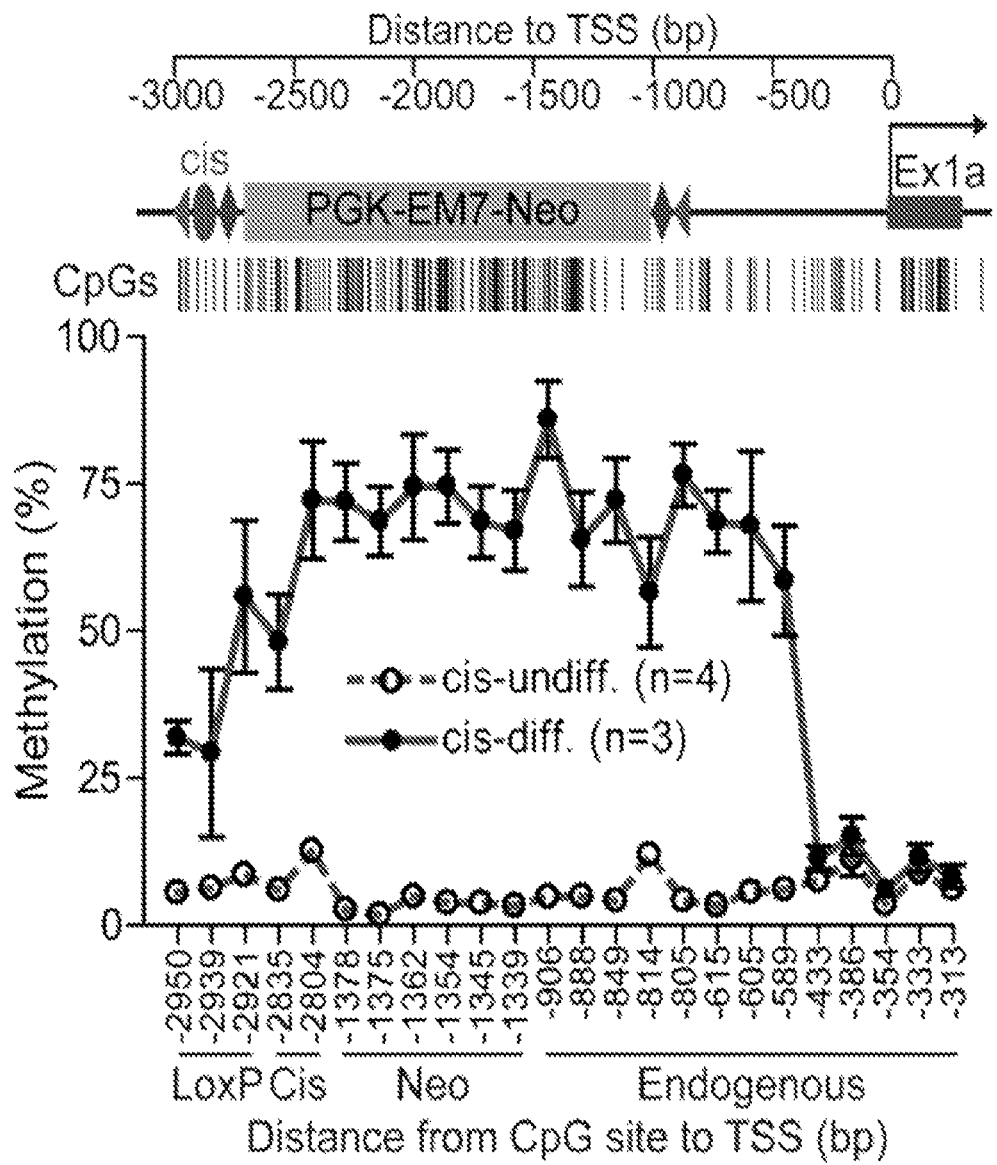
Figure 1C:
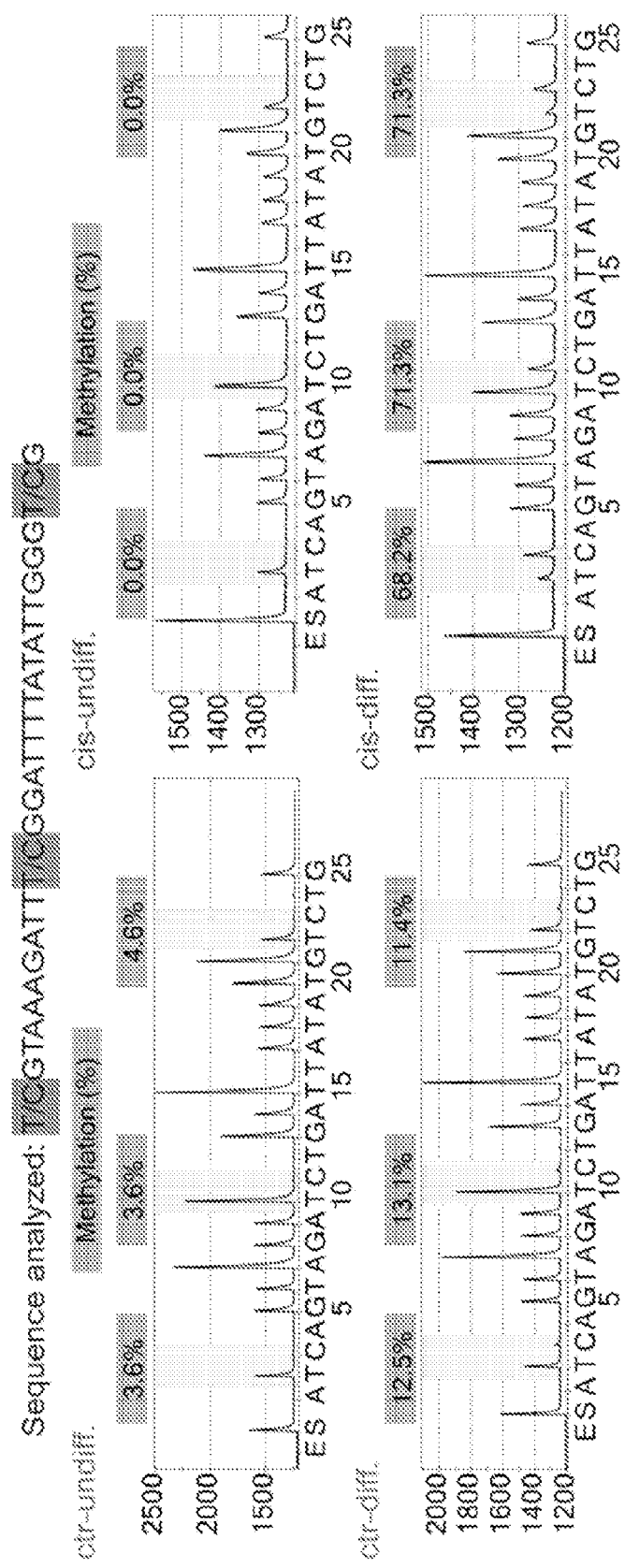
Figures 1D, 1E:
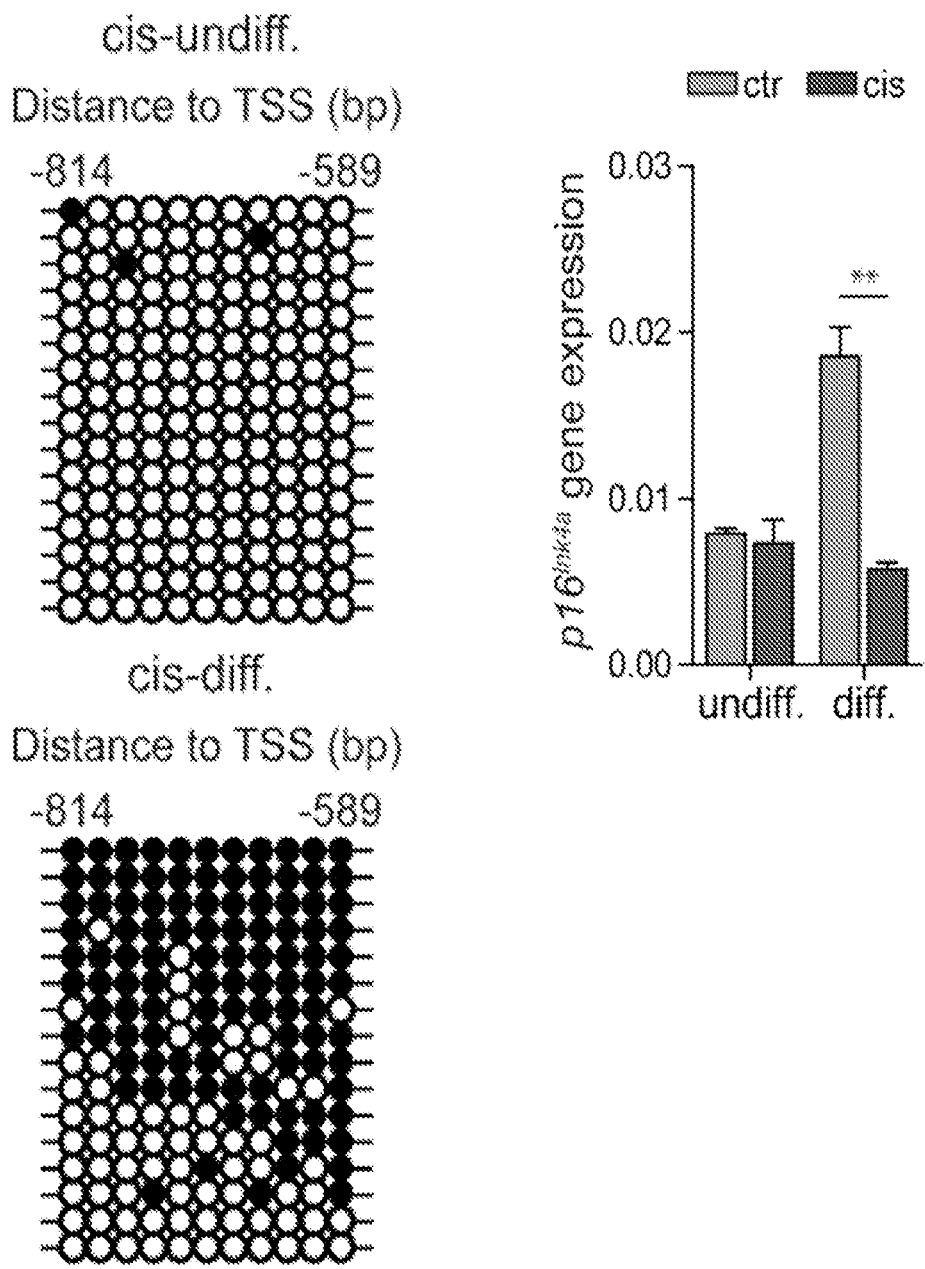
Figure 2A:
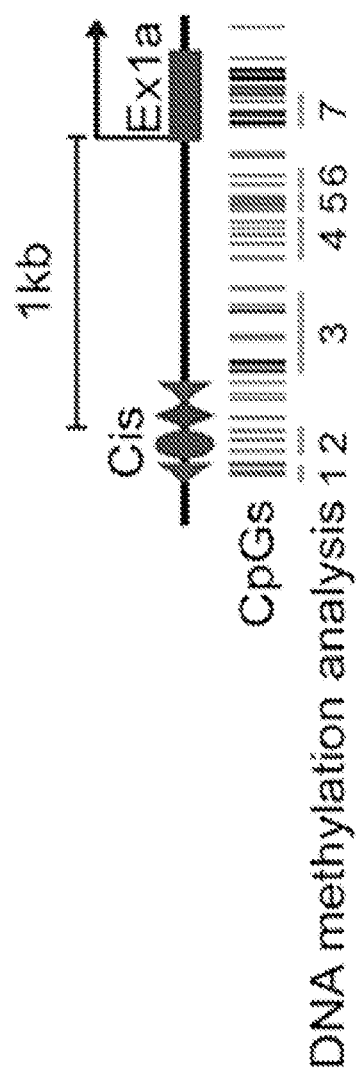
FIGS. 2A-2E: The cis-element induces p16 promoter methylation and age-dependent transcriptional suppression in vivo.
Figure 2C:
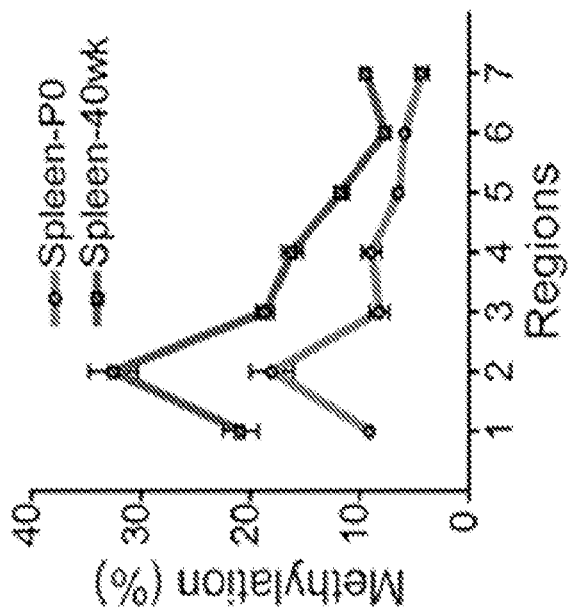
Figure 2B:
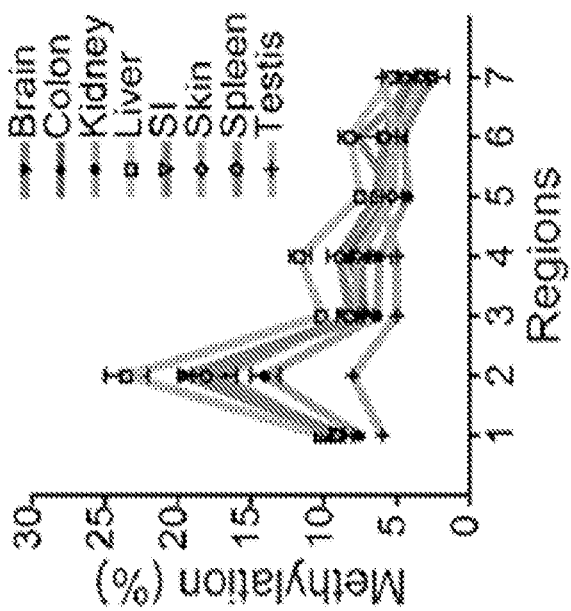
Figure 2D:
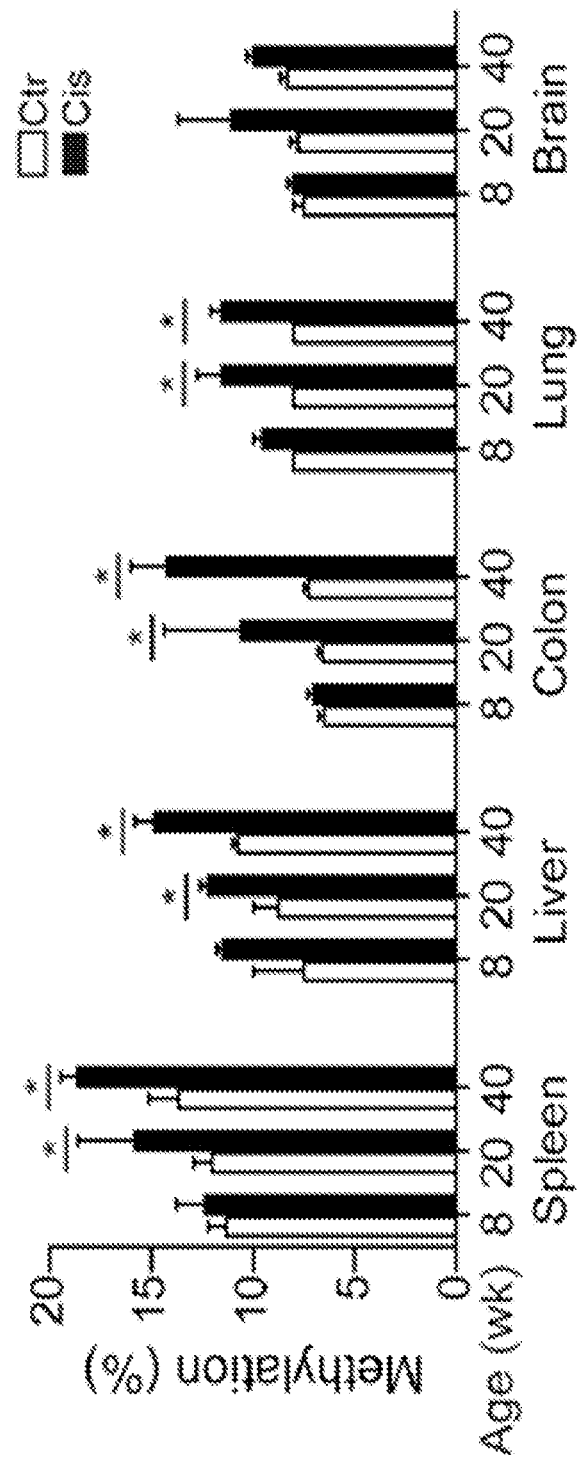
Figure 2E:
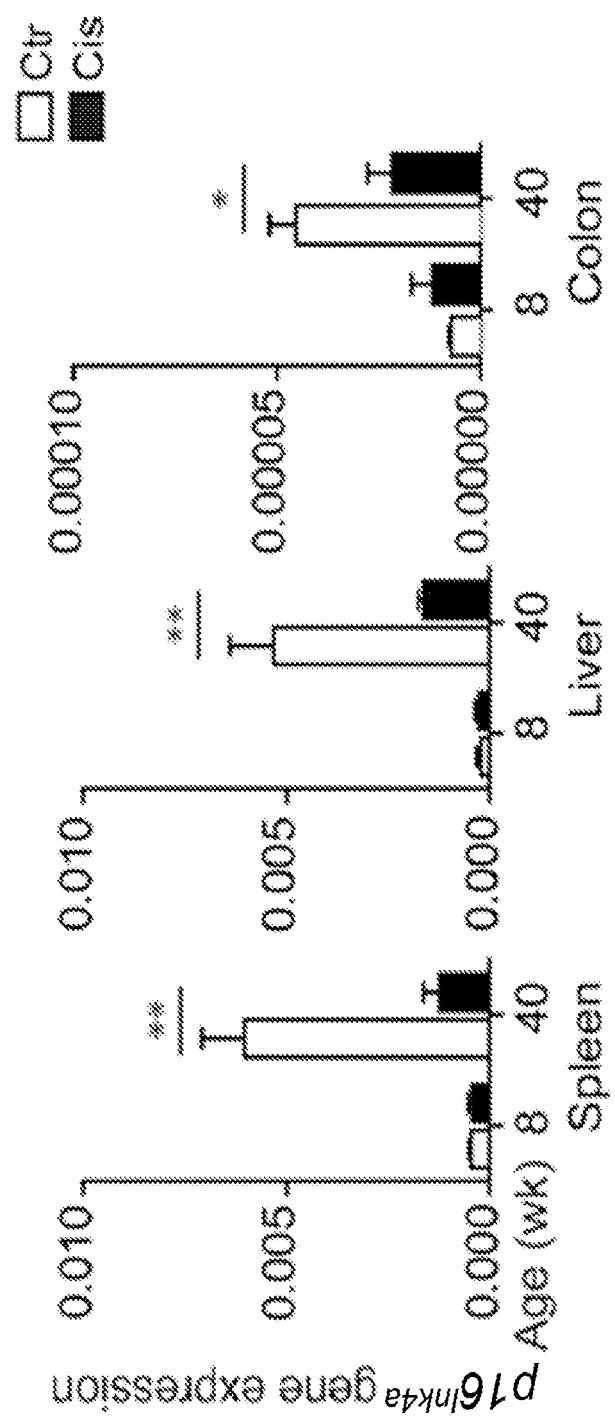

To initially determine whether the knock-in cis-element specifically induces DNA methylation at the endogenous p16 promoter, mESCs were studied in vitro. Differentiating ESCs recapitulate the earliest stages of embryonic lineage development. The progression of DNA methylation was analyzed before and after induced differentiation (25-26) in mESCs carrying either knock-in allele. To characterize the dynamics of methylation establishment, detailed methylation profiling was performed by quantitative bisulfite-pyrosequencing (27) at CpG sites spanning the knock-in sequence and the endogenous p16 promoter (−906 bp to −313 bp relative to TSS). Prior to differentiation, this region was essentially unmethylated in both control (ctr-undiff) and cis (cis-undiff) knock-in mESCs (FIG. 1). Upon differentiation of control mESCs (ctr-diff), a few CpG sites within the knock-in sequence showed modestly increased methylation, but methylation remained low at the endogenous p16 promoter (FIGS. 1A and 1C). In cis-element mESCs, conversely, differentiation (cis-diff) induced dramatically increased methylation both at the cis-element and at the p16 promoter (FIGS. 1B and 1C). These results clearly demonstrate that the cis-element attracts de novo methylation during differentiation, also affecting neighboring endogenous sequence. An independent method of assessing DNA methylation, bisulfite cloning and sequencing, confirmed extensive developmentally-regulated methylation in cis-element mESCs (FIG. 1D). Interestingly, methylation at the cis-targeted alleles exhibited clonal heterogeneity, suggesting it occurs in a cell-type specific fashion. Finally, to monitor the functional effects of induced methylation, p16 expression was assessed using quantitative TaqMan real-time RT-PCR (FIG. 1E). In control cells, p16 expression is up-regulated during differentiation, consistent with its functional role in limiting the replicative capacity of stem cells (28). In cis-element knock-in cells, however, induced promoter methylation during differentiation leads to strong transcriptional repression.

Figure 8:
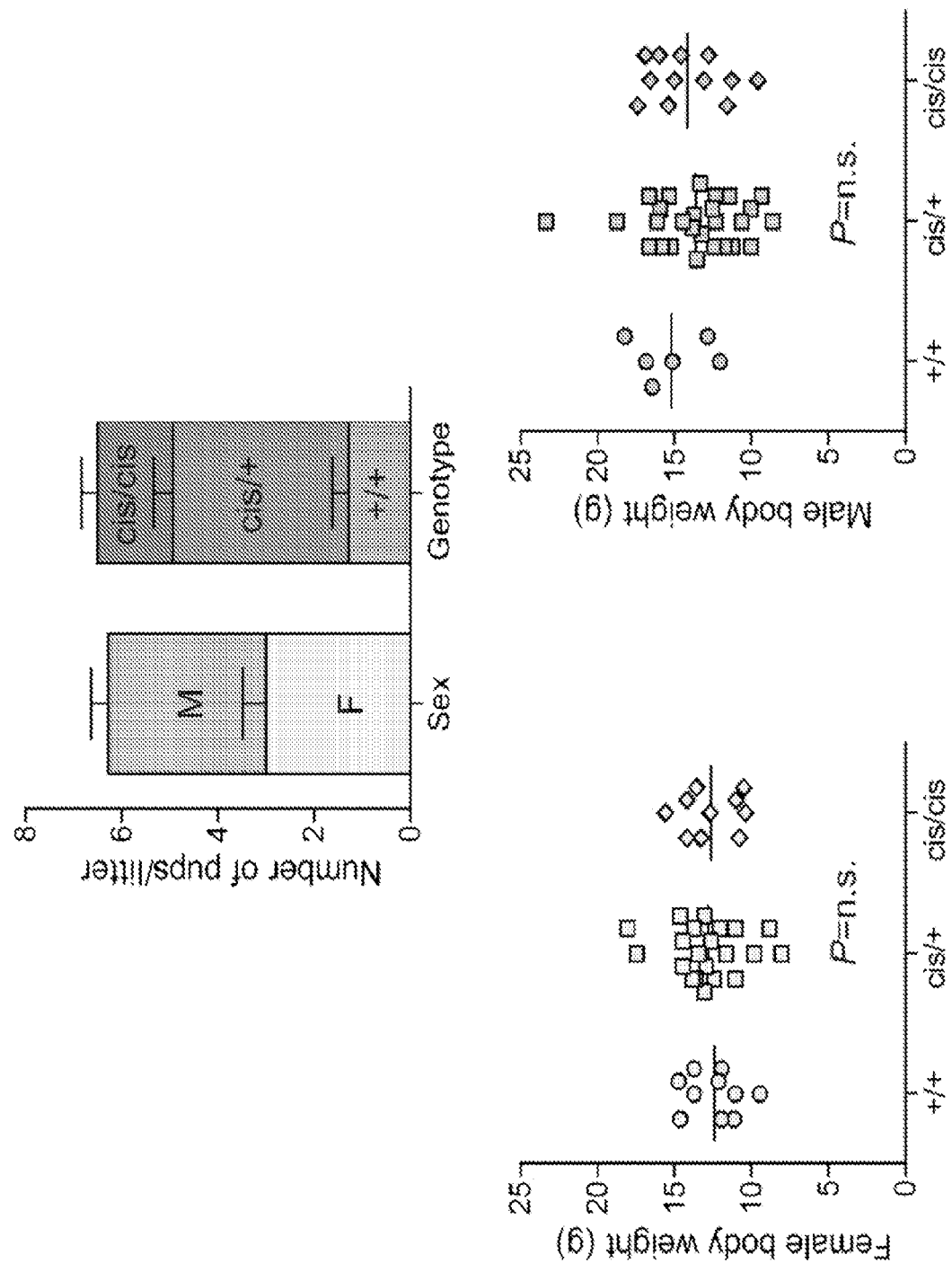
FIG. 8: Litter size, ratios of sex and genotype and body weight at weaning of pups from p16$_{cis}$ heterozygous intercrosses. F, female; and M, male. Results are means±SEM.
Figure 9:
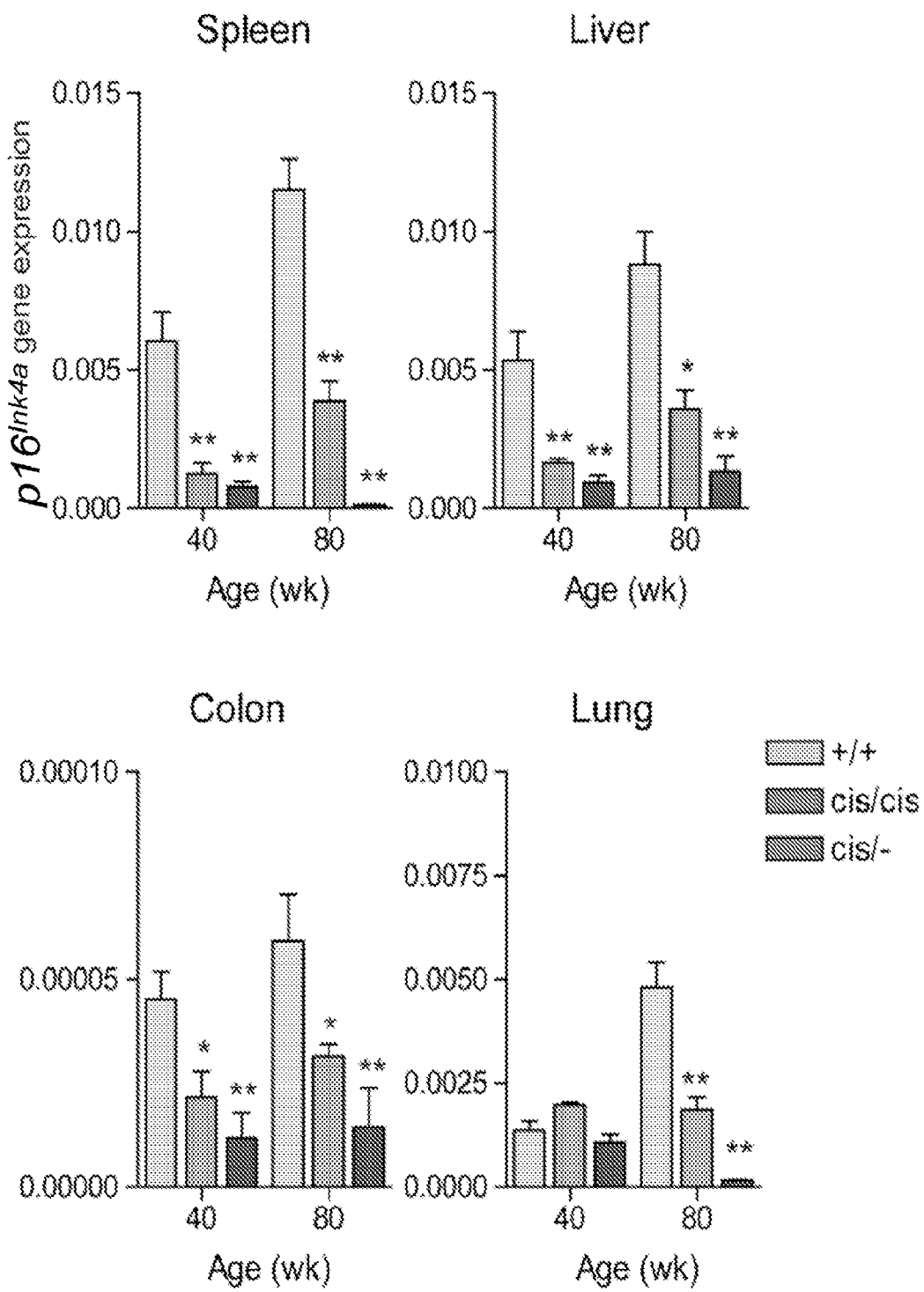
FIG. 9: Real-time p16 mRNA expression analysis in aging tissues. qRT-PCR of p16 expression shows that, in multiple tissues, the induction of p16 expression during aging was significantly repressed in the p16$_{cis/cis}$ and p16$_{cis/−}$ mice (n=3-5). *P<0.05 and **P<0.01 by Student's t test; error bars are ±SEM.

Having verified that the engineered cis-element specifically induces developmentally regulated promoter methylation and transcriptional silencing, p16 methylation was analyzed in multiple tissues from $p16^{cis}$ homozygous ($p16^{cis/cis}$) mice after excision of the Frt-flanked selection marker (FIG. 2). $p16^{cis/cis}$ mice are viable, fertile and do not display any gross physical or behavioral abnormalities (FIG. 8). In agreement with the data in differentiating mESCs, there was initial methylation seeding within the cis-element in almost all mouse tissues at birth (P0) (FIG. 2B). The notable exception is testis, in which there was low methylation at all CpG sites. This is remarkably consistent with previous observations, because the promoter CGIs with which the sequence motifs were originally associated are also highly methylated in most tissues except testis and sperm (23). With aging, cis-element mediated methylation spread toward the endogenous p16 promoter (FIG. 2C). In spleen, liver and colon, normal age-related increases in DNA methylation at the p16 promoter were significantly accelerated by the cis-element (FIG. 2D), with commensurate reductions in gene expression (FIG. 2E). Collectively, these results demonstrate that our approach successfully induces developmentally regulated somatic p16 epimutation, leading to transcriptional repression in vivo.

Figure 3A:
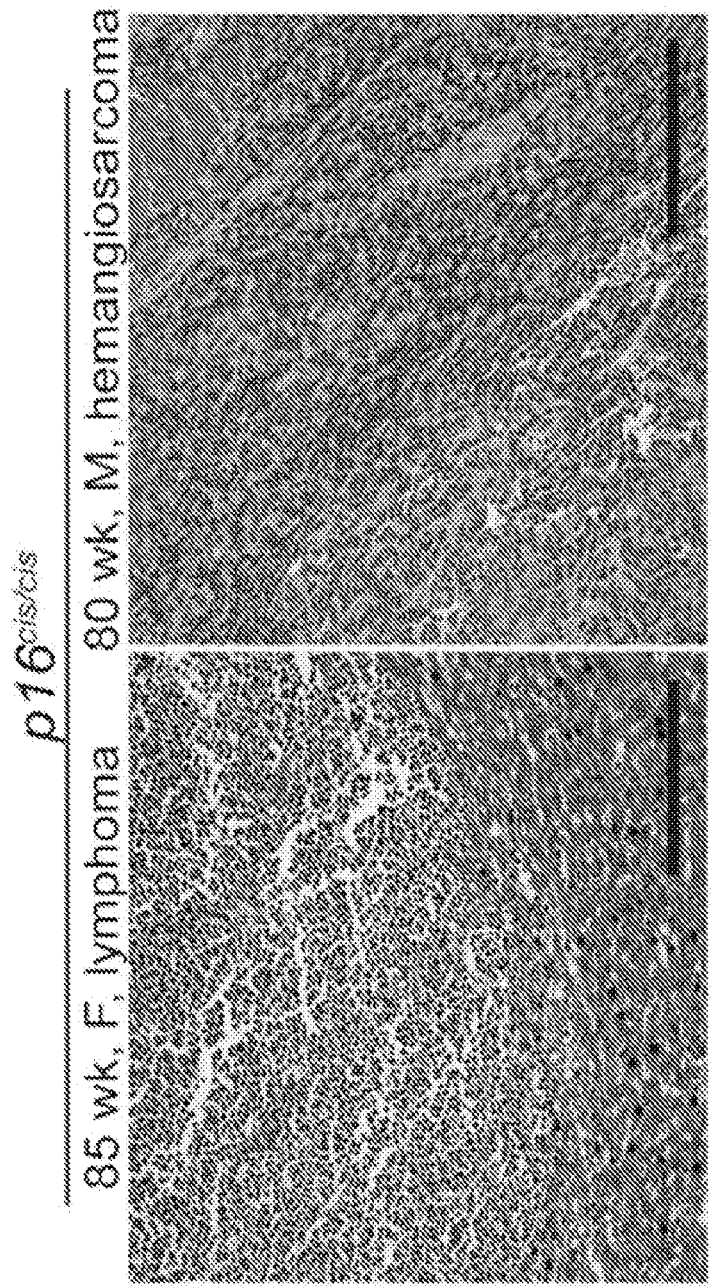
FIGS. 3A-3F: The driving role of p16 epimutation in tumorigenesis in vivo. Representative histological appearance of malignancies in $p16_{cis/cis}$ (FIG. 3A) and $p16_{cis/−}$ mice (FIG. 3B). Mouse age, sex and tumor type are indicated. Scale bars represent 200 µm.
Figure 3B:
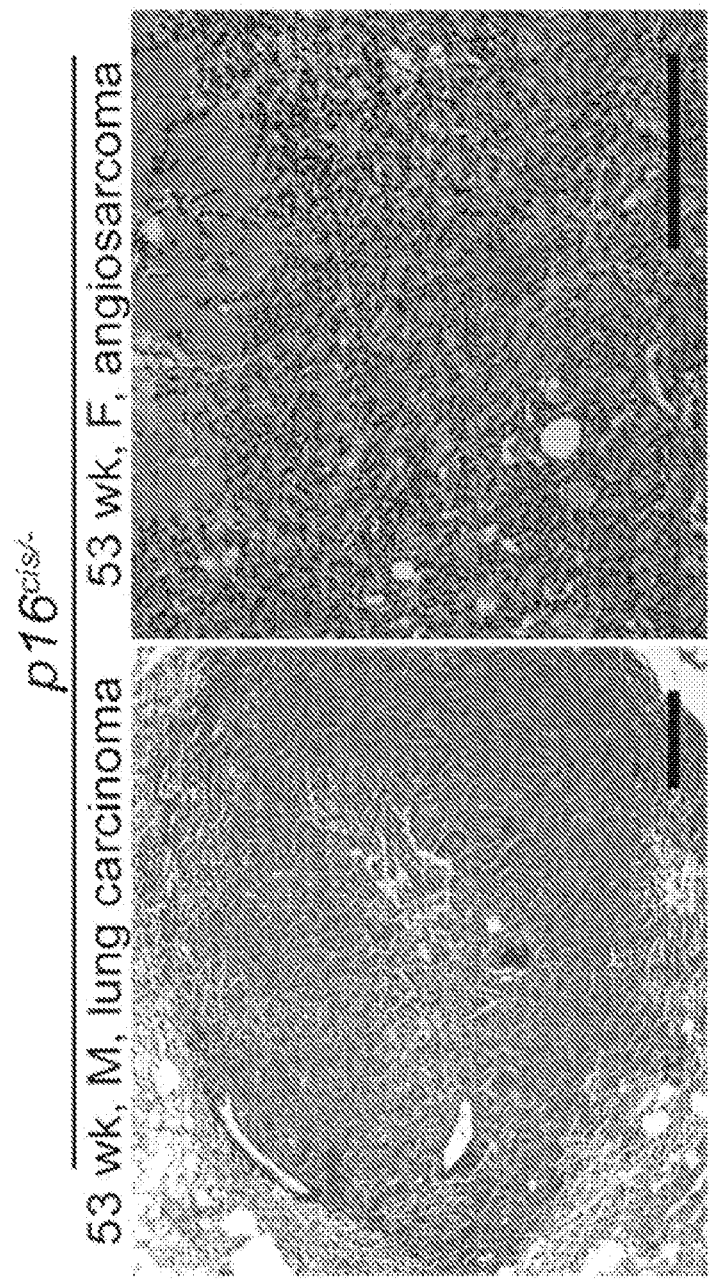
Figure 3D:
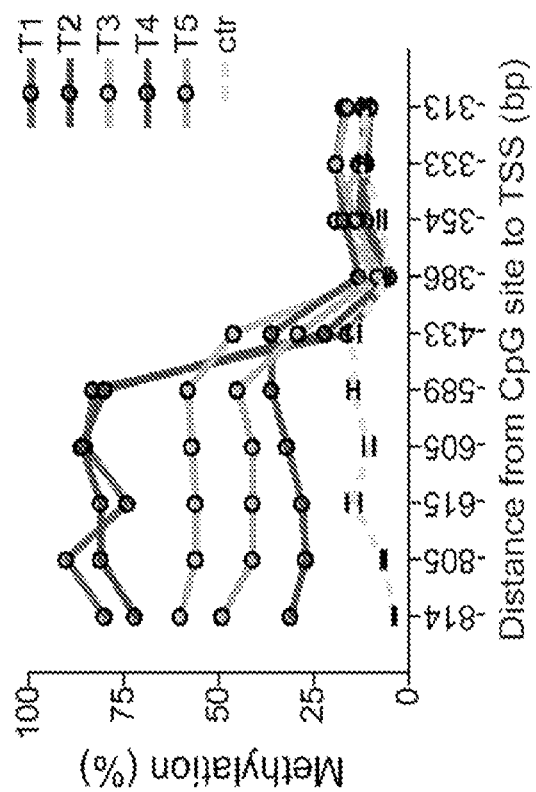
Figure 3C:
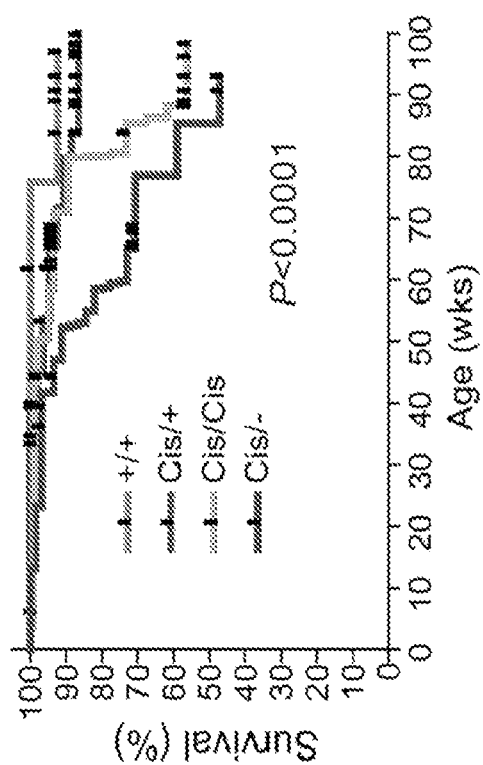
Figure 3E:
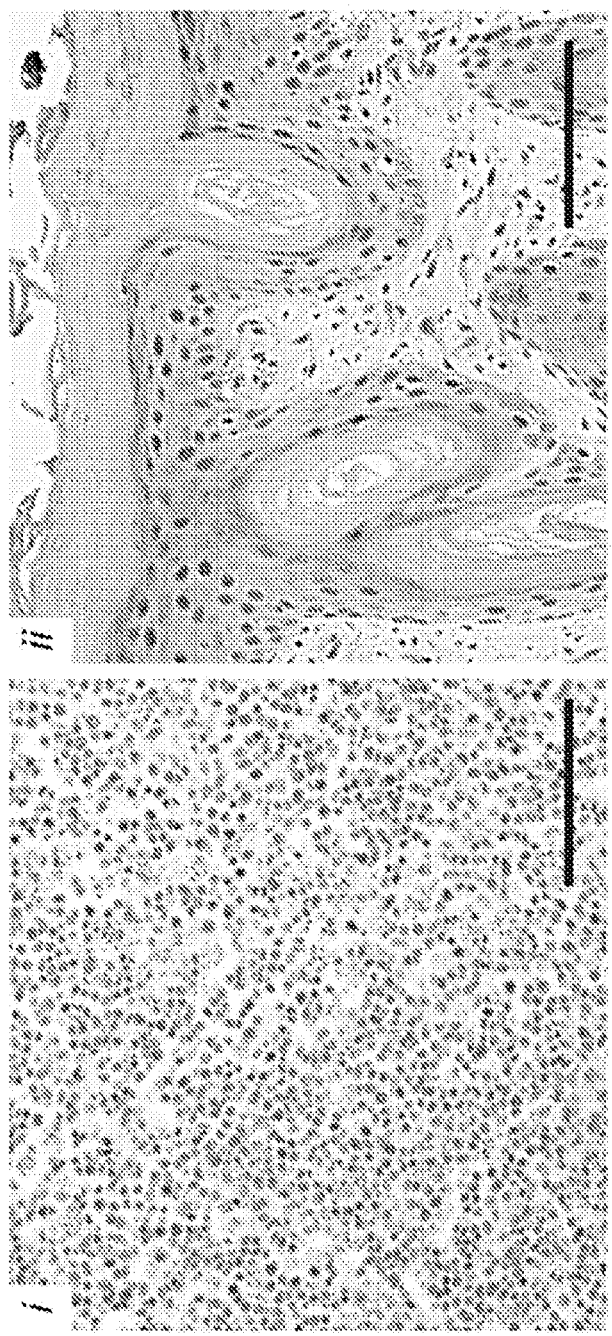
Figure 3F:
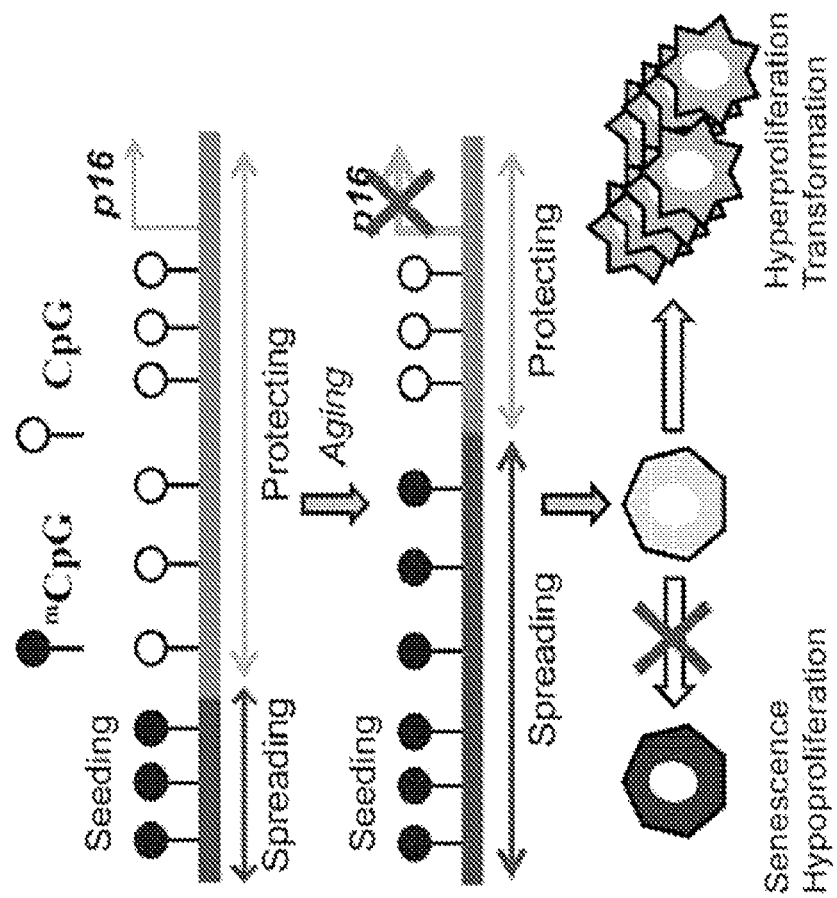
Figures 11B, 11C, 11E, 11F, 11H, 11I:
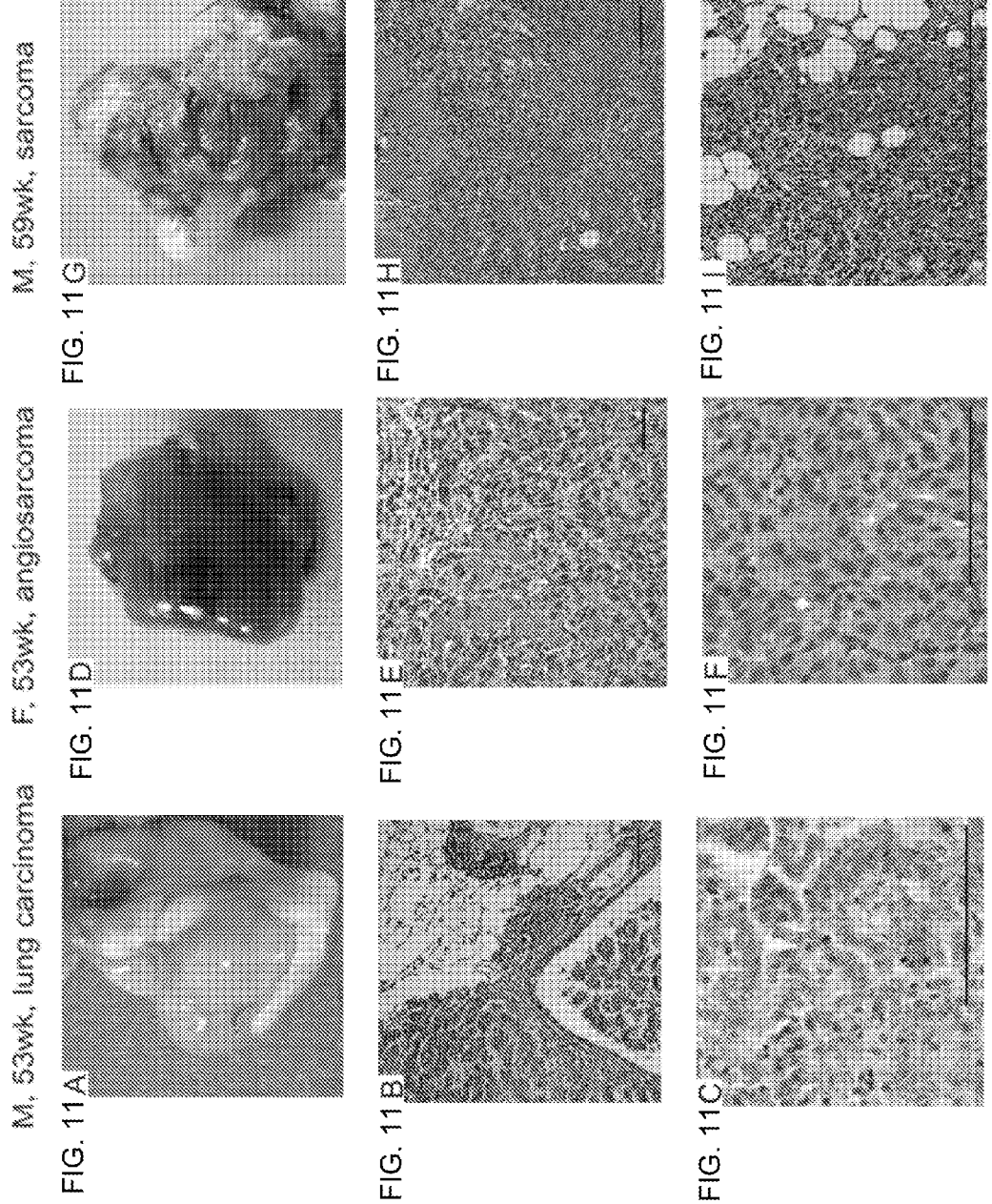
Figure 12:
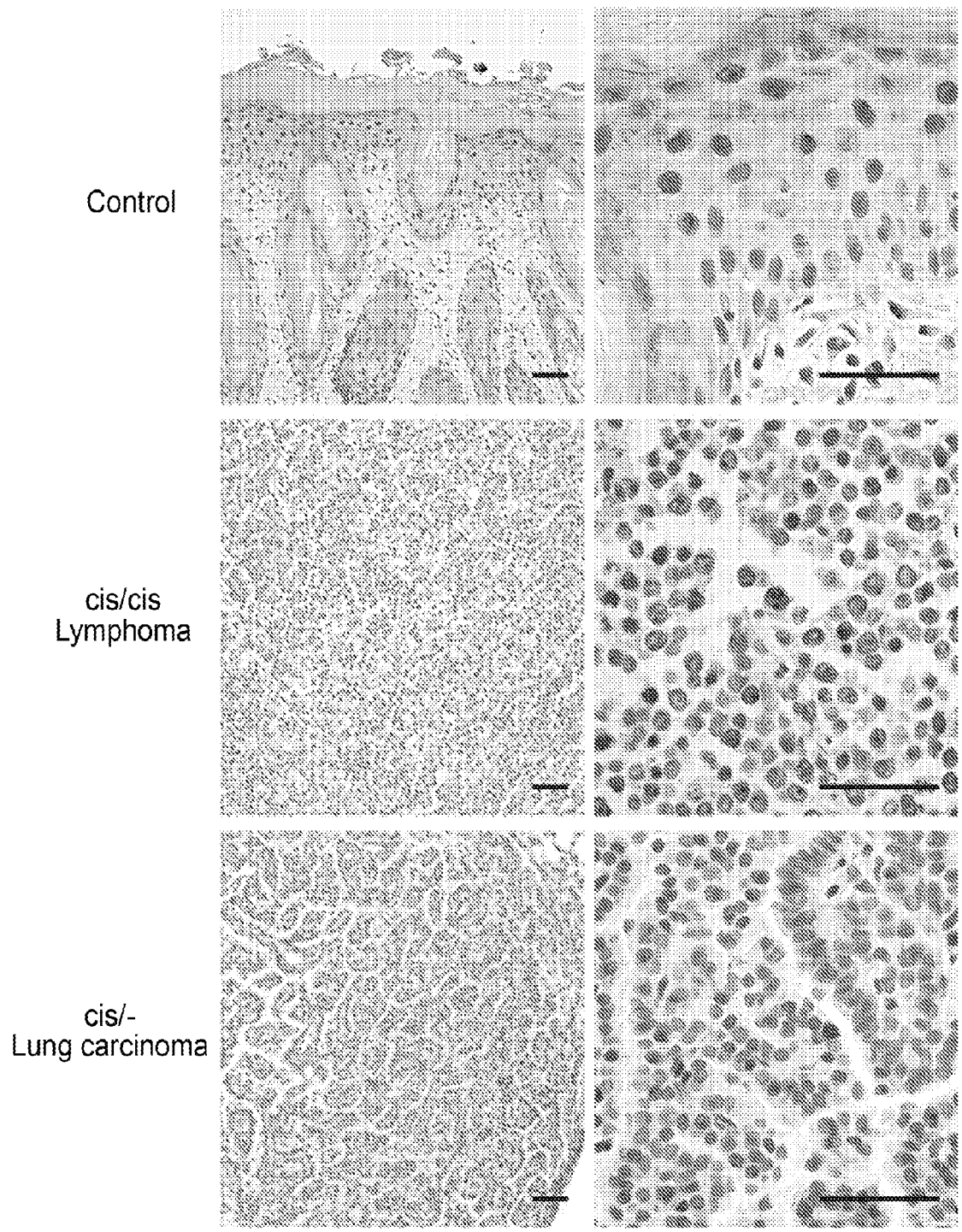
FIG. 12: Immunohistochemical analysis of p16 expression in tumors collected from p16$_{cis/cis}$ and p16$_{cis/−}$ mice. Immunohistochemistry confirms the lack of p16 expression in the transformed tumor cells. For each staining, there is a magnified view on the right panel. Scale bars equal 50 μm.

To test whether p16 promoter methylation predisposes animals to tumor development, heterozygous intercrossing was used to generate a cohort of $p16^{+/+}$, $p16^{+/cis}$ and $p16^{cis/cis}$ mice (on a mixed 129/C57 genetic background) and monitored tumor development and survival. In mice aged 35-100 weeks (wks), 0 (0%) of 18 $p16^{+/+}$ mice, 1 (2%) of 51 $p16^{+/cis}$ mice, and 4 (18%) of 22 $p16^{cis/cis}$ mice developed spontaneous tumors. One $p16^{+/cis}$ mouse died at age 72 wks and a neck sarcoma was detected at necropsy (FIGS. 10A-10C). The malignancies in $p16^{cis/cis}$ mice were either lymphoma or sarcoma (FIG. 3A and FIGS. 10D-10I). Given that p16 deficiency in many human cancers involves mutation of one allele and promoter hypermethylation of the other (29), it was next assessed the cooperative tumorigenic effects of combined p16 mutation and epimutation. To this end, the $p16^{cis}$ allele was bred into mice on a p16 exon1α deletion background (30) to generate $p16^{cis/\Delta exon1\alpha}$ mice (designated $p16^{cis/-}$, on a mixed FVB/129/C57 background). In 20 $p16^{cis/-}$ mice aged 40-91 wks, 6 (30%) tumors were found; the malignancies were sarcoma (3), lung carcinoma (2), or lymphoma (1) (FIG. 3B and FIG. 11). Moreover, consistent with p16 epimutation serving as one of Knudson's two-hits, $p16^{cis/-}$ mice had accelerated tumor onset and significantly shortened survival (FIG. 3C). To ascertain the role of p16 promoter methylation in the oncogenic pathway in vivo, we performed quantitative analyses of p16 promoter methylation and gene expression in the tumor tissues. Hypermethylation of the p16 promoter in tumors (FIG. 3D) was associated with essentially complete loss of protein expression (FIG. 3E and FIG. 12). Taken together, the results provide direct evidence for a driving role of p16 epigenetic silencing by promoter hypermethylation in tumor formation and progression (FIG. 3F).

In conclusion, these studies provide the first clear demonstration that p16 epimutation causes tumorigenesis. Embodiments of the disclosure provide a novel mouse model and includes the testing of targeted epigenetic therapies for prevention and treatment of human cancer. The straightforward approach to 'epigenetic engineering' should be useful in testing the causal role of other epigenetic alterations implicated in carcinogenesis, and broadly applicable toward elucidating epigenetic etiology in a wide range of diseases.

Example 2

Exemplary Methods and Materials

Generation of Targeted Knock-in Mouse Strains.

A standard targeting method (31) was used to generate germline insertions of either control-element or cis-element upstream of the mouse p16 promoter. Correct targeting of exon 1α was confirmed by Southern blotting, PCR and DNA sequencing analysis. Once germ-line transmission was confirmed, heterozygous mice were bred with germline Flp recombinase expressing mice (32) to remove the Neo selection cassette.

DNA Methylation and Gene Expression Analysis.

Quantitative bisulfite-pyrosequencing for DNA methylation analyses was performed as previously described (33). Bisulfite sequencing of cloned PCR products was used to confirm methylation of CpG sites. TaqMan quantitative real-time RT-PCR was carried out for mouse p16 as previously described (34) and relative gene expression was normalized to β-Actin.

Immunohistochemistry.

Tissue processing and immunohistochemistry were performed using a previously described procedure (35). The primary antibody, anti-p16 (Santa Cruz), was used at 1:100 dilution.

Statistics.

Student's t tests with two-tailed distribution were used to determine the significance of difference. $P<0.05$ was considered statistically significant.

Study Approval.

All animals were treated in accordance with the NIH Guide for Care and Use of Laboratory Animals as approved by the Baylor College of Medicine Animal Care committee.

Figure 5A:
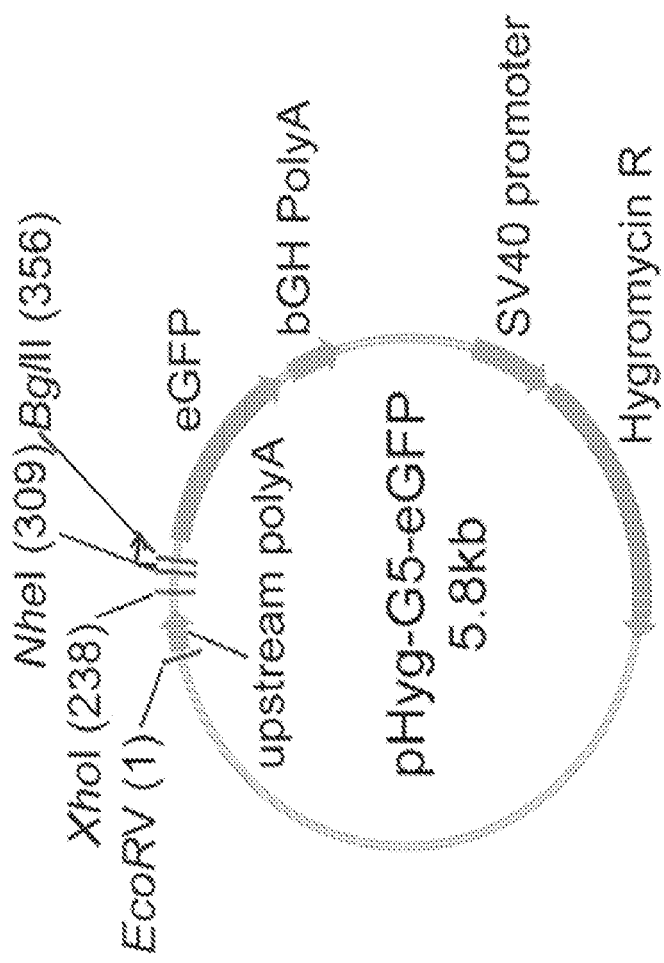
FIGS. 5A-5E: Cis-element induces CGI methylation on the INSL6 transgene.
Figure 5B:
Figure 5C:
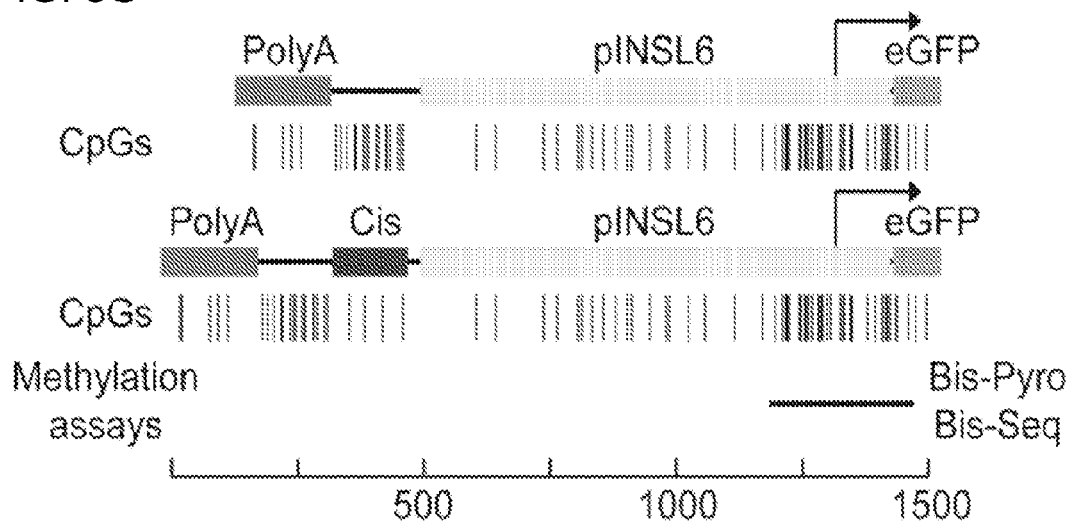
Figure 5D:
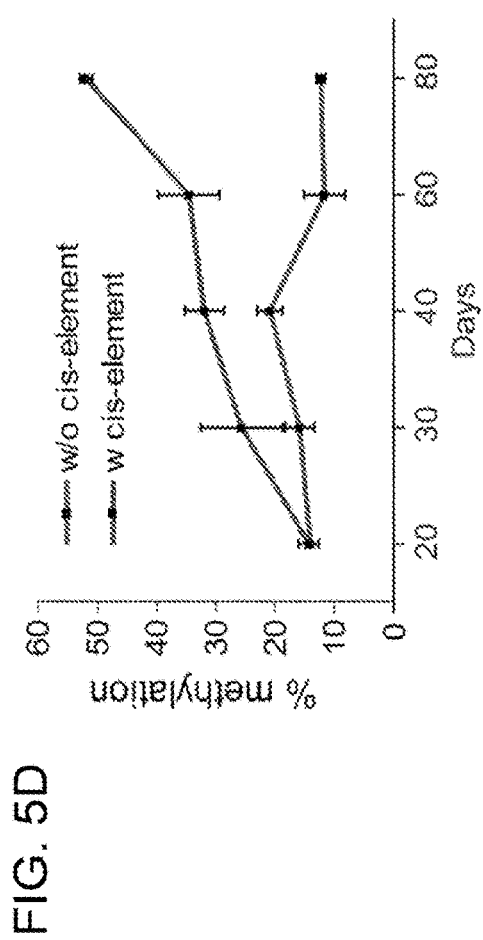
Figure 5E:
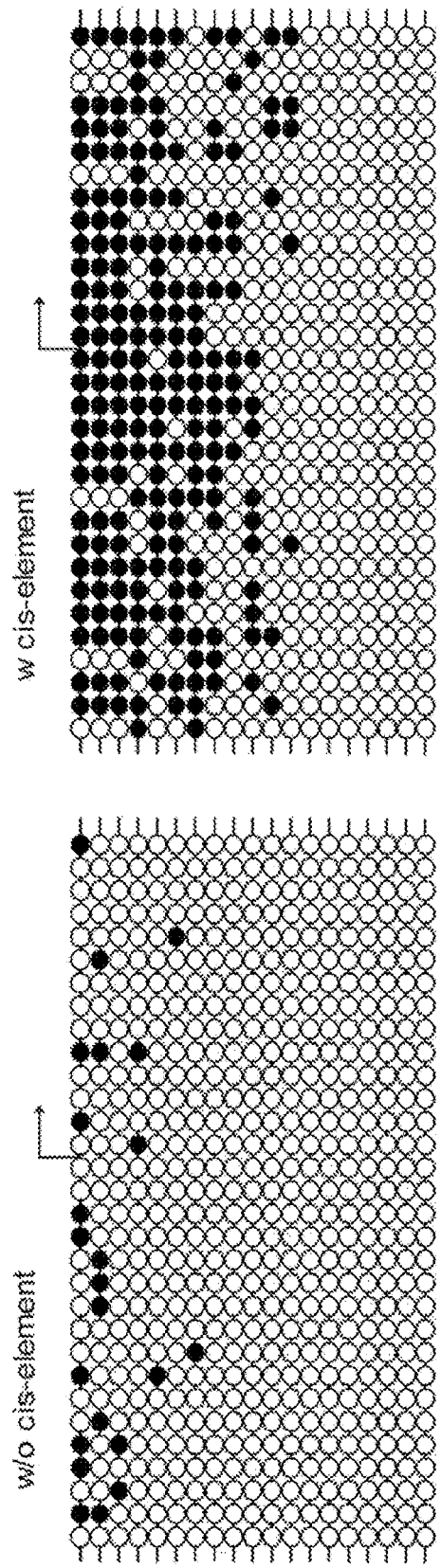
Figure 6A:
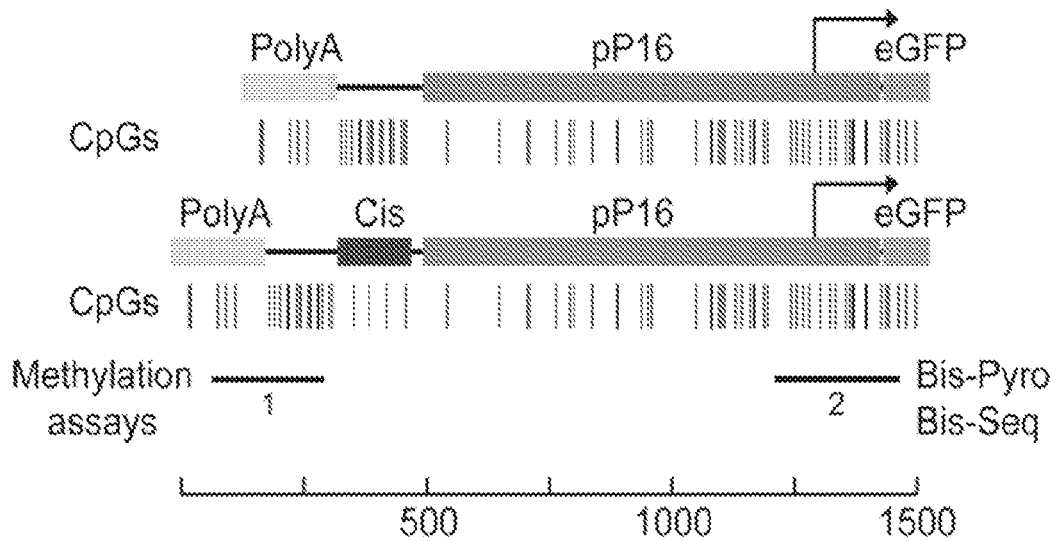
FIGS. 6A-6D: Cis-element induces CGI methylation on the p16 transgenes.
Figure 6B:
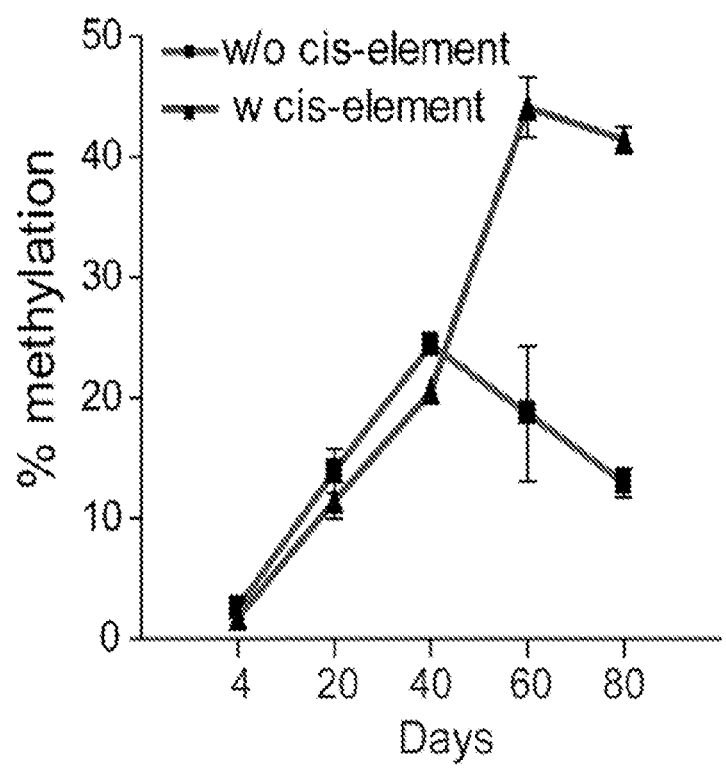
Figure 6C:
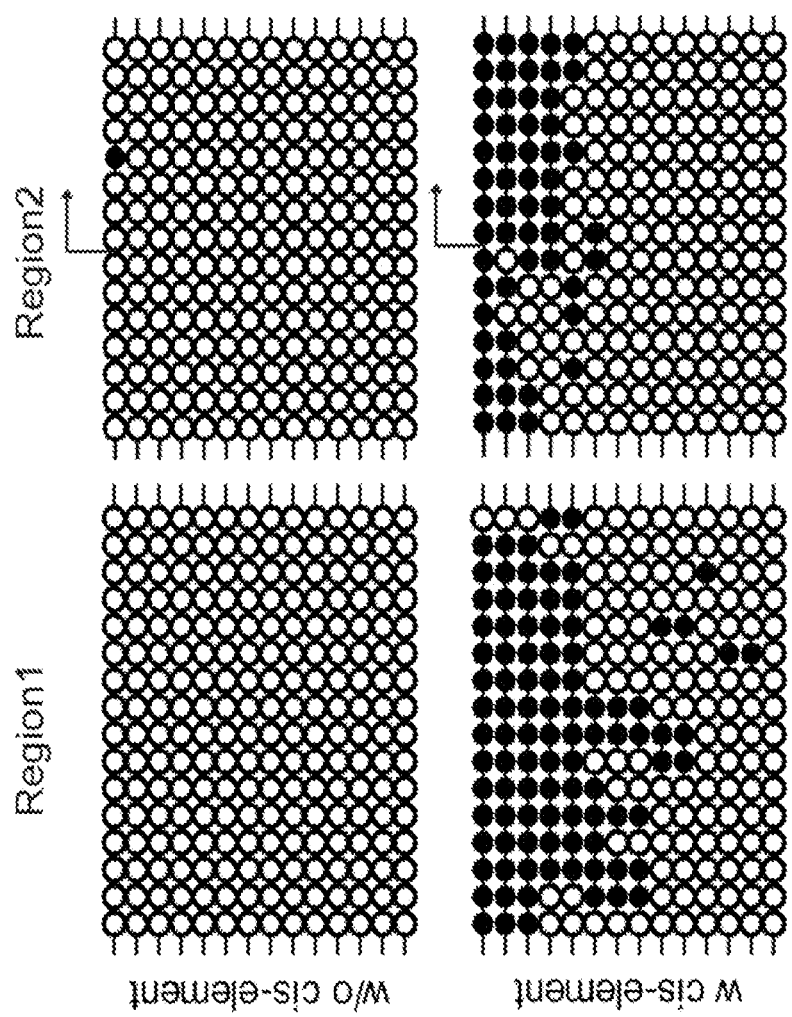
Figure 6D:
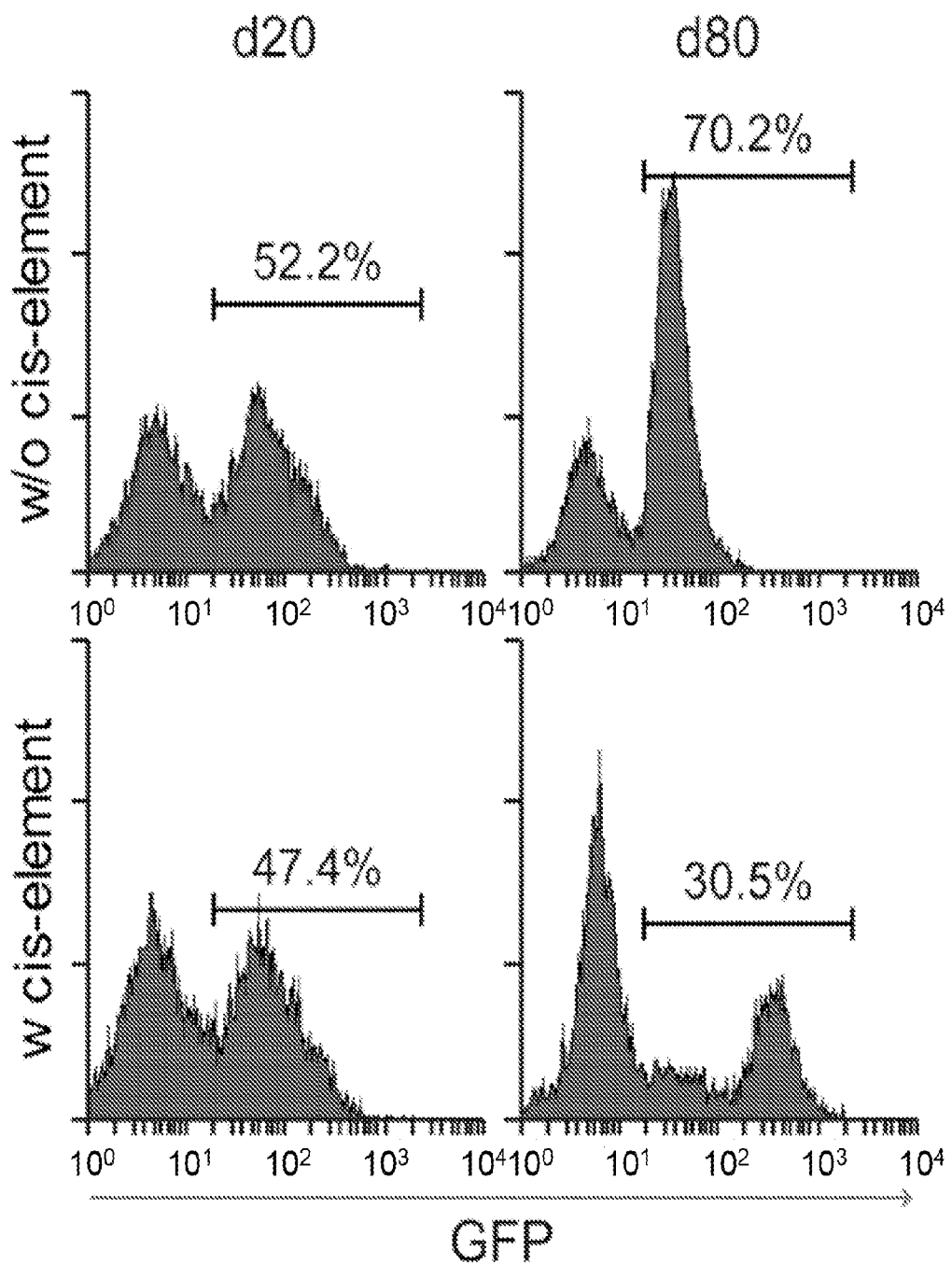
Figure 7A:
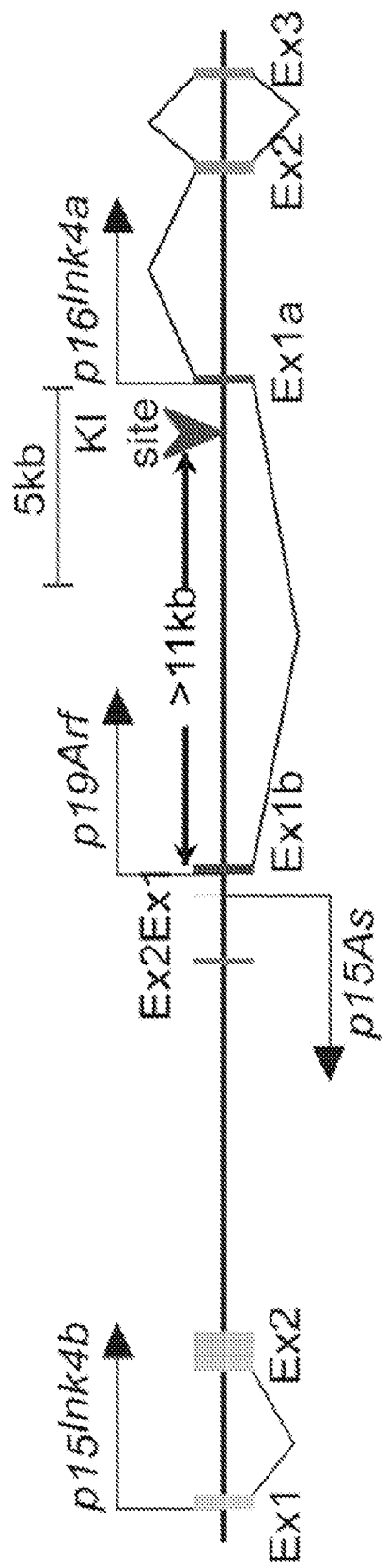
FIGS. 7A-7D: Targeted knock-in of control or cis-elements upstream of mouse p16 promoter.
Figure 7B:
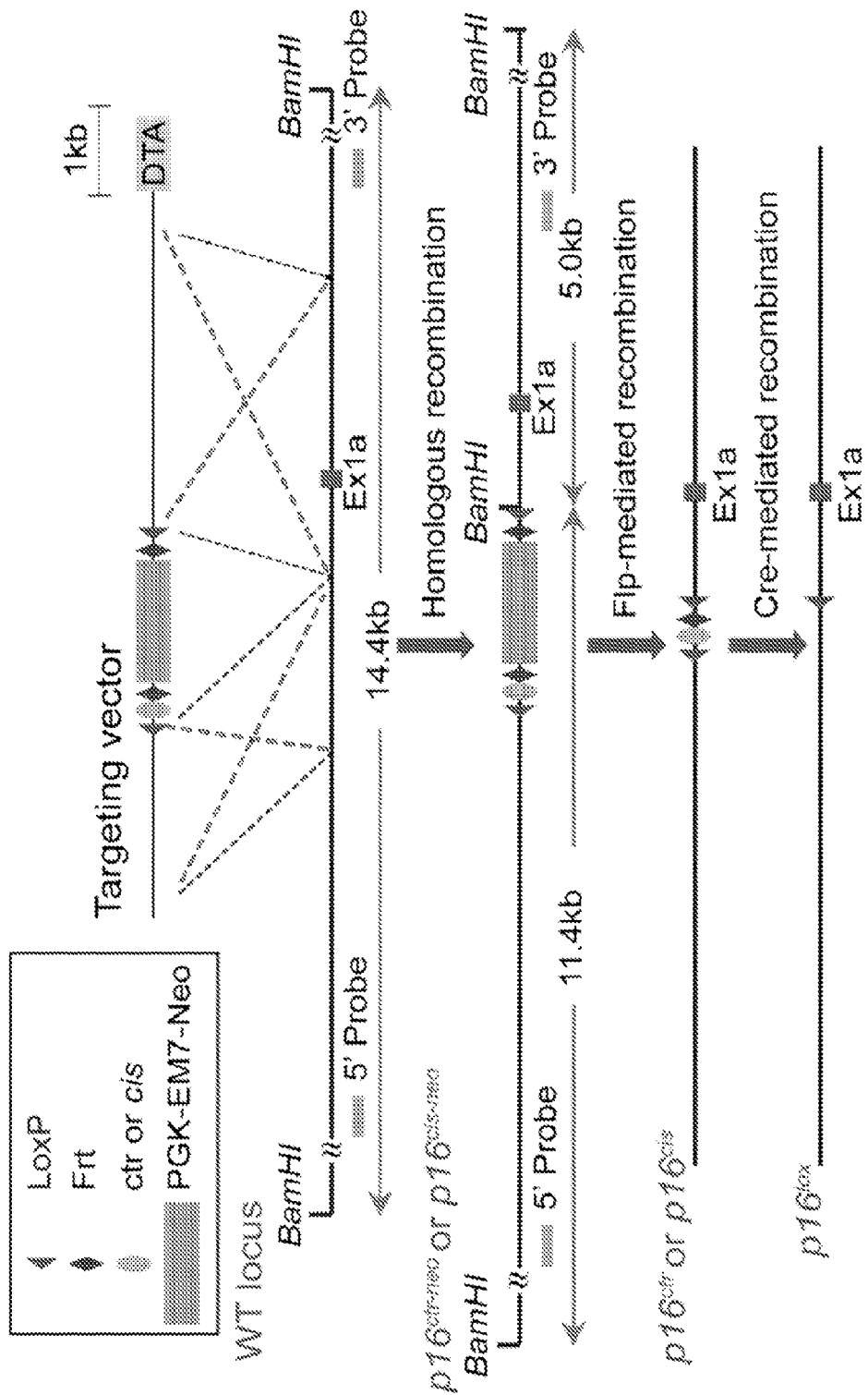
Figure 7C:
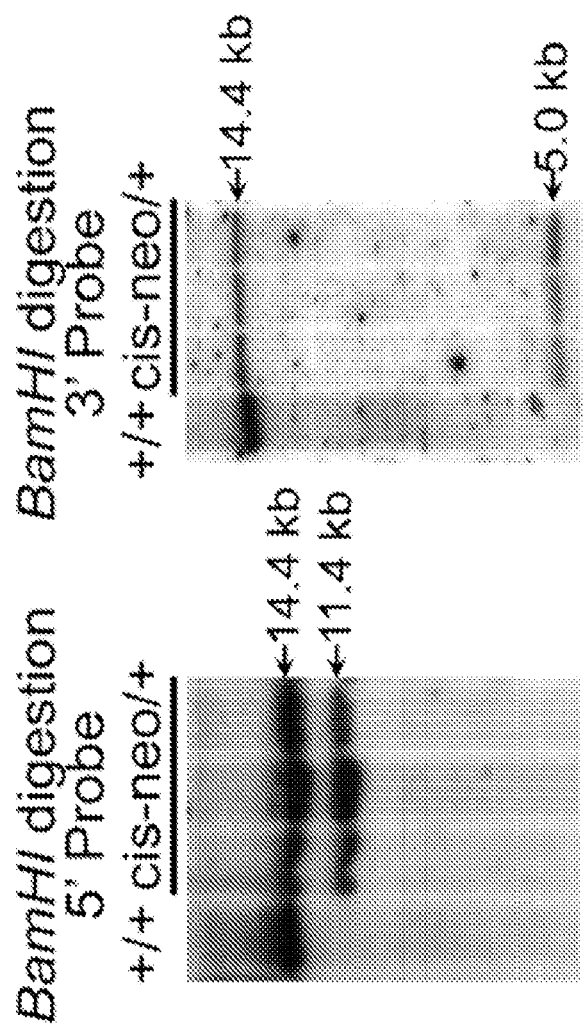
Figure 7D:
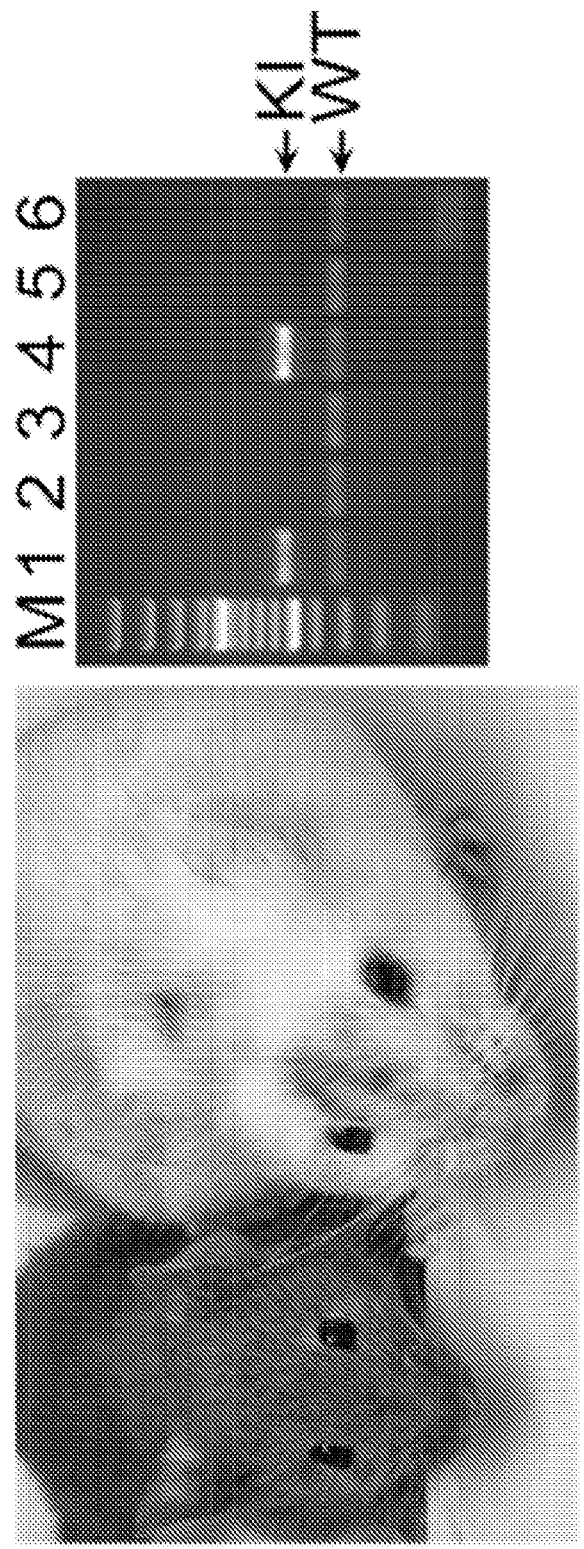

Stable transgene experiments. Two transgenes were constructed: one containing a promoter CGI of human INSL6 gene, which is methylated and silenced in tissue-specific manner (23), and the second containing a promoter CGI of human p16 gene, which is frequently methylated in cancer cells. The pHyg-G5-eGFP vector was used for transfection. It carries a Hygromycin resistance gene and an eGFP reporter gene (FIG. 5A). A NheI/BglII fragment containing either the INSL6 promoter (900 bp) or p16 promoter (882 bp) was PCR amplified from normal genomic DNA and cloned into the vector in front of eGFP. To generate the construct containing the cis-element, a NheI/XhoI fragment containing the 140 bp cis-element was oligo synthesized and inserted in front of the promoters. Plasmids were linearized (with or without cis-element) with EcoRV (FIG. 5B) and individually transfected into a human prostate cancer cell line LNCaP and a mouse fibroblast cell line NIH3T3. The transfected cells were selected with 200 µg/ml hygromycin for 7 days. The surviving cells were then pooled and cultured in selection free medium. Cells were collected every 10 days and analyzed for DNA methylation of the integrated plasmids by bisulfite-pyrosequencing and clonal bisulfite-sequencing. The transfection and methylation analysis experiments were independently repeated three times.

Targeted Knock-in Experiments.

A standard targeting method was used to generate germline insertions of either control-element or cis-element upstream of the mouse p16 promoter. Gap repair method (31) was used to isolate a p16 genomic clone suitable for the construction of a targeting vector. Briefly, a BAC clone was obtained (carrying $Cm_R$) derived from 129 mouse strain containing p16 from the Sanger Center. Two homologous fragments of ~500 bp each were PCR amplified from the BAC DNA and cloned into a pDTA vector which included a diphtheria toxin A gene (DTA) as a negative selection marker. The resulting pDTA vector was linearized and introduced into a homologous recombination proficient *E. coli* strain (SW105). The transformed cells were plated on Lysogeny Broth containing the antibiotic ampicillin (LB/Amp). Only recombinants survived Amp selection. To insert the sequences, homologous recombination was used as described (31). The scheme is shown in FIG. 7. First, a recombinogenic fragment was constructed consisting of the following (5' to 3'): 500 bp sequence homologous to the sequence 5' to the site of insertion, LoxP, control or cis elements, Frt, PKG-Em7-Neo, Frt, LoxP, and 500 bp sequence homologous to the sequence 3' to the site of insertion. This fragment was released from its vector and recombined with the p16 genomic clone. EM7 is a synthetic promoter functional in *E. coli*, making Neo a dual marker. To modify one allele of p16, the linearized targeting construct was introduced into mouse ESCs at Mouse ES Cell Core Facility at the Baylor College of Medicine.

Southern Blot, DNA Sequencing and Genotyping Assays.

For Southern blotting, 20 µg genomic DNA was digested with BamHI, resolved on a 0.7% agarose gel, transferred to nylon membranes and hybridized with P32-dCTP-labelled 5' and 3' probes. For PCR and DNA sequencing analysis, the knock-in region was amplified from genomic DNA by using the forward primer (5'-TTTAAATCCTCCCTTCTGTCCA-3' [SEQ ID NO: 7]) and the reverse primer (5'-AGAGTTACCAGGGATCCACCTAAT-3' [SEQ ID NO:8]). The PCR product was directly sequenced using the same primers at Sequencing Core Facility at the Baylor College of Medicine. To facilitate genotyping, multiplex PCR (three primers in one reaction) were used to detect the presence of the endogenous and knock-in alleles.

Generation of Targeted Knock-in Mouse Strains.

Three recombinant mES clones were injected into C57BL/6J blastocysts to generate chimeric mice at the Genetically Engineered Mouse Core Facility at Baylor College of Medicine. Chimeric mice were crossed onto the C57BL/6J background and successful germline transmission was confirmed in the offspring by both Southern blotting and DNA sequencing.

DNA Methylation Analysis.

Primer sequences and PCR conditions for quantitative bisulfite-pyrosequencing are summarized in Supplemental Table 2. For each assay, set-up included positive controls (SssI-treated genomic DNA) and negative controls (whole genome amplified genomic DNA), mixing experiments to rule out bias, and repeated experiments to assess reproducibility. Annealing temperatures were optimized to overcome PCR bias as previously reported (33). For clonal bisulfite sequencing analysis, post-bisulfite PCR products were cloned into the TA vector pCR4-TOPO (Invitrogen), plasmid DNA was extracted from 15-20 clones with the use of a QIAprep Spin Miniprep kit (Qiagen), and the DNA was sequenced at Sequencing Core Facility at the Baylor College of Medicine.

Gene Expression Analysis by Real-Time RT-PCR.

TaqMan qRT-PCR was carried out in triplicate for mouse p16 as previously described (34). This assay was designed to have primers/probes to specifically span p16 exon-exon junctions. Relative gene expression was calculated by the ratio of the target genes to β-Actin (Mm00607939_s1) expression on an ABI StepOnePlus Detection System.

Histology and Immunohistochemistry.

For histological analyses, mouse tissues were fixed in 4% paraformaldehyde. Fixed tissues were paraffin-embedded, sectioned, and stained with haematoxylin and eosin according to standard laboratory protocols at the Cellular and Molecular Morphology Core at the Texas Medical Center Digestive Disease Center. Immunohistochemical staining was performed for p16 protein on paraffin-embedded tissue sections as previously described (35). Briefly, 5-µm-thick sections were deparaffinized, rehydrated, incubated with incubated with 3% $H_2O_2$ to block endogenous peroxidase activity, and incubated with normal sheep serum to block nonspecific antibody binding. The sections were incubated at 4° C. overnight with a monoclonal antibody against p16 protein (1:100 dilution; Santa Cruz), followed by incubation with anti-biotin secondary antibody (Vector laboratories) diluted in 1:1000. Slides were developed using DAB kit (Vector laboratories), and imaged using a DS-Fi1 camera connected to Nikon E80i stereomicroscope. Images were processed using Nikon imaging software, NIS Elements RA3.2. p16 expression in nuclei was scored as present or absent.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

1. Holliday R. The inheritance of epigenetic defects. Science. 1987; 238(4824):163-70.
2. Feinberg A P, and Tycko B. The history of cancer epigenetics. Nat Rev Cancer. 2004; 4(2):143-53.

3. Baylin S B, and Jones P A. A decade of exploring the cancer epigenome—biological and translational implications. Nat Rev Cancer. 2011; 11(10):726-34.
4. Shen L, Ahuja N, Shen Y, Habib N A, Toyota M, Rashid A, and Issa JP. DNA methylation and environmental exposures in human hepatocellular carcinoma. J Natl Cancer Inst. 2002; 94(10):755-61.
5. Shen L, Toyota M, Kondo Y, Lin E, Zhang L, Guo Y, Hernandez N S, Chen X, Ahmed S, Konishi K, et al. Integrated genetic and epigenetic analysis identifies three different subclasses of colon cancer. Proc Natl Acad Sci USA. 2007; 104(47):18654-9.
6. Shen L, Catalano P J, Benson A B, 3rd, O'Dwyer P, Hamilton S R, and Issa J P. Association between DNA methylation and shortened survival in patients with advanced colorectal cancer treated with 5-fluorouracil based chemotherapy. Clin Cancer Res. 2007; 13(20): 6093-8.
7. Shen L, Kantarjian H, Guo Y, Lin E, Shan J, Huang X, Berry D, Ahmed S, Zhu W, Pierce S, et al. DNA methylation predicts survival and response to therapy in patients with myelodysplastic syndromes. J Clin Oncol. 2010; 28(4):605-13.
8. Baylin S, and Bestor T H. Altered methylation patterns in cancer cell genomes: cause or consequence? Cancer Cell. 2002; 1(4):299-305.
9. Laird P W. The power and the promise of DNA methylation markers. Nat Rev Cancer. 2003; 3(4):253-66.
10. Issa J P, Ottaviano Y L, Celano P, Hamilton S R, Davidson N E, and Baylin SB. Methylation of the oestrogen receptor CpG island links ageing and neoplasia in human colon. Nat Genet. 1994; 7(4):536-40.
11. Sharpless N E, and DePinho R A. The INK4A/ARF locus and its two gene products. Curr Opin Genet Dev. 1999; 9(1):22-30.
12. Herman J G, Merlo A, Mao L, Lapidus R G, Issa J P, Davidson N E, Sidransky D, and Baylin SB. Inactivation of the CDKN2/p16/MTS1 gene is frequently associated with aberrant DNA methylation in all common human cancers. Cancer Res. 1995; 55(20):4525-30.
13. Issa J P, Ahuja N, Toyota M, Bronner M P, and Brentnall T A. Accelerated age-related CpG island methylation in ulcerative colitis. Cancer Res. 2001; 61(9):3573-7.
14. Kondo Y, Kanai Y, Sakamoto M, Mizokami M, Ueda R, and Hirohashi S. Genetic instability and aberrant DNA methylation in chronic hepatitis and cirrhosis—A comprehensive study of loss of heterozygosity and microsatellite instability at 39 loci and DNA hypermethylation on 8 CpG islands in microdissected specimens from patients with hepatocellular carcinoma. Hepatology. 2000; 32(5): 970-9.
15. Nuovo G J, Plaia T W, Belinsky S A, Baylin S B, and Herman J G. In situ detection of the hypermethylation-induced inactivation of the p16 gene as an early event in oncogenesis. Proc Natl Acad Sci USA. 1999; 96(22): 12754-9.
16. Belinsky S A, Nikula K J, Palmisano W A, Michels R, Saccomanno G, Gabrielson E, Baylin S B, and Herman J G. Aberrant methylation of p16(INK4a) is an early event in lung cancer and a potential biomarker for early diagnosis. Proc Natl Acad Sci USA. 1998; 95(20):11891-6.
17. Maegawa S, Hinkal G, Kim H S, Shen L, Zhang L, Zhang J, Zhang N, Liang S, Donehower L A, and Issa J P. Widespread and tissue specific age-related DNA methylation changes in mice. Genome Res. 2010; 20(3):332-40.
18. Nishida N, Nagasaka T, Nishimura T, Ikai I, Boland C R, and Goel A. Aberrant methylation of multiple tumor suppressor genes in aging liver, chronic hepatitis, and hepatocellular carcinoma. Hepatology. 2008; 47(3):908-18.
19. Waki T, Tamura G, Tsuchiya T, Sato K, Nishizuka S, and Motoyama T. Promoter methylation status of E-cadherin, hMLH1, and p16 genes in nonneoplastic gastric epithelia. Am J Pathol. 2002; 161(2):399-403.
20. Baylin S B, and Ohm J E. Epigenetic gene silencing in cancer—a mechanism for early oncogenic pathway addiction? Nat Rev Cancer. 2006; 6(2):107-16.
21. Lienert F, Wirbelauer C, Som I, Dean A, Mohn F, and Schubeler D. Identification of genetic elements that autonomously determine DNA methylation states. Nat Genet. 2011.
22. Yates P A, Burman R W, Mummaneni P, Krussel S, and Turker M S. Tandem B1 elements located in a mouse methylation center provide a target for de novo DNA methylation. J Biol Chem. 1999; 274(51):36357-61.
23. Shen L, Kondo Y, Guo Y, Zhang J, Zhang L, Ahmed S, Shu J, Chen X, Waterland R A, and Issa J P. Genome-wide profiling of DNA methylation reveals a class of normally methylated CpG island promoters. PLoS Genet. 2007; 3(10):2023-36.
24. Zhang Y, Shu J, Si J, Shen L, Estecio M R, and Issa J P. Repetitive elements and enforced transcriptional repression co-operate to enhance DNA methylation spreading into a promoter CpG-island. Nucleic Acids Res. 2012; 40(15):7257-68.
25. Bibel M, Richter J, Lacroix E, and Barde Y A. Generation of a defined and uniform population of CNS progenitors and neurons from mouse embryonic stem cells. Nat Protoc. 2007; 2(5): 1034-43.
26. McKinney-Freeman S, and Daley G. Derivation of hematopoietic stem cells from murine embryonic stem cells. J Vis Exp. 20072):162.
27. Shen L, Guo Y, Chen X, Ahmed S, and Issa J P. Optimizing annealing temperature overcomes bias in bisulfite PCR methylation analysis. Biotechniques. 2007; 42(1):48-58.
28. Li H, Collado M, Villasante A, Strati K, Ortega S, Canamero M, Blasco M A, and Serrano M. The Ink4/Arf locus is a barrier for iPS cell reprogramming. Nature. 2009; 460(7259):1136-9.
29. Rocco J W, and Sidransky D. p16(MTS-1/CDKN2/INK4a) in cancer progression. Exp Cell Res. 2001; 264 (1):42-55.
30. Sharpless N E, Bardeesy N, Lee K H, Carrasco D, Castrillon D H, Aguirre A J, Wu E A, Homer J W, and DePinho R A. Loss of p16Ink4a with retention of p19Arf predisposes mice to tumorigenesis. Nature. 2001; 413 (6851):86-91.
31. Zhang P, Li M Z, and Elledge S J. Towards genetic genome projects: genomic library screening and gene-targeting vector construction in a single step. Nat Genet. 2002; 30(1):31-9.
32. Farley F W, Soriano P, Steffen L S, and Dymecki S M. Widespread recombinase expression using FLPeR (flipper) mice. Genesis. 2000; 28(3-4):106-10.
33. Shen L, Guo Y, Chen X, Ahmed S, and Issa J P. Optimizing annealing temperature overcomes bias in bisulfite PCR methylation analysis. Biotechniques. 2007; 42(1):48, 50, 2 passim.

34. Krishnamurthy J, Torrice C, Ramsey M R, Kovalev G I, Al-Regaiey K, Su L, and Sharpless N E. Ink4a/Arf expression is a biomarker of aging. J Clin Invest. 2004; 114(9):1299-307.
35. Yu D H, Ware C, Waterland R A, Zhang J, Chen M H, Gadkari M, Kunde-Ramamoorthy G, Nosavanh L M, and Shen L. Developmentally programmed 3' CpG island methylation confers tissue- and cell-type-specific transcriptional activation. Mol Cell Biol. 2013; 33(9):1845-58.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An engineered cell comprising a recombinant pro-methylation cis-element construct, wherein said element resides in a regulatory region of a target gene, wherein the cis-element comprises a sequence that is at least 80%, 85%, 90%, 95%, 97%, or 99% identical to SEQ ID NO:1.

2. The cell of claim 1, wherein the cis-element comprises SEQ ID NO:1.

3. An engineered cell comprising a recombinant pro-methylation cis-element construct, wherein said element resides in a regulatory region of a target gene, and wherein the cis-element comprises a sequence that is at least 80%, 85%, 90%, 95%, 97%, or 99% identical to SEQ ID NO:3.

4. An engineered cell comprising a recombinant pro-methylation cis-element construct, wherein said element resides in a regulatory region of a target gene, and wherein the cis-element comprises a sequence that is at least 80%, 85%, 90%, 95%, 97%, or 99% identical to SEQ ID NO:4.

5. An engineered cell comprising a recombinant pro-methylation cis-element construct, wherein said element resides in a regulatory region of a target gene, and wherein the cis-element comprises a sequence that is at least 80%, 85%, 90%, 95%, 97%, or 99% identical to SEQ ID NO:6.

6. The cell of claim 5, wherein the cis-element comprises SEQ ID NO:6.

7. The cell of claim 1, wherein the cell is a mammalian cell.

8. The cell of claim 1, wherein the cell is a stem cell.

9. The cell of claim 8, wherein the stem cell is an embryonic stem cell.

10. The cell of claim 1, wherein the cell is a somatic cell.

11. The cell of claim 1, wherein the cell is a germ cell.

12. The cell of claim 1, wherein the cell is not a cell of the testis or sperm.

13. The cell of claim 1, wherein the construct comprises site-directed recombination elements.

14. The cell of claim 13, wherein the site-directed recombination elements comprise Cre-Lox elements, Flp-FRT elements, PKG-Em7-Neo, or a combination thereof.

15. The cell of claim 1, wherein the construct lacks a sequence that encodes a DNA methyltransferase.

16. A plurality of the cell of claim 1.

17. The cell of claim 3, wherein the cis-element comprises SEQ ID NO:3.

18. The cell of claim 3, wherein the construct comprises site-directed recombination elements.

19. The cell of claim 18, wherein the site-directed recombination elements comprise Cre-Lox elements, Flp-FRT elements, PKG-Em7-Neo, or a combination thereof.

20. The cell of claim 3, wherein the construct lacks a sequence that encodes a DNA methyltransferase.

21. A plurality of the cell of claim 3.

22. The cell of claim 4, wherein the cis-element comprises SEQ ID NO:4.

23. The cell of claim 4, wherein the construct comprises site-directed recombination elements.

24. The cell of claim 23, wherein the site-directed recombination elements comprise Cre-Lox elements, Flp-FRT elements, PKG-Em7-Neo, or a combination thereof.

25. The cell of claim 4, wherein the construct lacks a sequence that encodes a DNA methyltransferase.

26. A plurality of the cell of claim 4.

27. The cell of claim 5, wherein the construct comprises site-directed recombination elements.

28. The cell of claim 27, wherein the site-directed recombination elements comprise Cre-Lox elements, Flp-FRT elements, PKG-Em7-Neo, or a combination thereof.

29. The cell of claim 5, wherein the construct lacks a sequence that encodes a DNA methyltransferase.

30. A plurality of the cell of claim 5.

* * * * *

```
                        SEQUENCE LISTING

<160> NUMBER OF SEQ ID NOS: 8

<210> SEQ ID NO 1
<211> LENGTH: 13
<212> TYPE: DNA
<213> ORGANISM: Artificial Sequence
<220> FEATURE:
<223> OTHER INFORMATION: Synthetic Primer

<400> SEQUENCE: 1
gctgaggcag gag                                                        13

<210> SEQ ID NO 2
<211> LENGTH: 13
<212> TYPE: DNA
<213> ORGANISM: Artificial Sequence
<220> FEATURE:
<223> OTHER INFORMATION: Synthetic Primer

<400> SEQUENCE: 2
ctcctgcctc agc                                                        13

<210> SEQ ID NO 3
<211> LENGTH: 15
<212> TYPE: DNA
<213> ORGANISM: Artificial Sequence
<220> FEATURE:
<223> OTHER INFORMATION: Synthetic Primer

<400> SEQUENCE: 3
actaaaaata caaaa                                                      15

<210> SEQ ID NO 4
<211> LENGTH: 11
<212> TYPE: DNA
<213> ORGANISM: Artificial Sequence
<220> FEATURE:
<223> OTHER INFORMATION: Synthetic Primer

<400> SEQUENCE: 4
cactccagcc t                                                          11

<210> SEQ ID NO 5
<211> LENGTH: 11
<212> TYPE: DNA
<213> ORGANISM: Artificial Sequence
<220> FEATURE:
<223> OTHER INFORMATION: Synthetic Primer

<400> SEQUENCE: 5
```

```
aggctggagt g                                                            11

<210> SEQ ID NO 6
<211> LENGTH: 140
<212> TYPE: DNA
<213> ORGANISM: Artificial Sequence
<220> FEATURE:
<223> OTHER INFORMATION: Synthetic Primer

<400> SEQUENCE: 6
atcccagcta cttgggaggc tgaggcagga gaatcacgga tccagcctgg ccaacatggt      60
gaaaacccgt ctctactaaa aatacaaaaa ttaaagctta gatcgtgtca ctgcactcca    120
gcctgggtga cagagcaaga                                                 140

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
tttaaatcct cccttctgtc ca                                               22

<210> SEQ ID NO 8
<211> LENGTH: 24
<212> TYPE: DNA
<213> ORGANISM: Artificial Sequence
<220> FEATURE:
<223> OTHER INFORMATION: Synthetic Primer

<400> SEQUENCE: 8
agagttacca gggatccacc taat                                             24
```